US010955407B2

(12) United States Patent
Boess et al.

(10) Patent No.: US 10,955,407 B2
(45) Date of Patent: Mar. 23, 2021

(54) IN VITRO TOXICITY SCREENING ASSAY

(71) Applicant: Roche Innovation Center Copenhagen A/S, Horsholm (DK)

(72) Inventors: Franziska Boess, Basel (CH); Sabine Sewing, Basel (CH); Annie Moisan, Basel (CH); Adrian B. Roth, Basel (CH); Cristina Bertinetti-Lapatki, Basel (CH)

(73) Assignee: Roche Innovation Center Copenhagen A/S, Basel (CH)

( * ) Notice: Subject to any disclaimer, the term of this patent is extended or adjusted under 35 U.S.C. 154(b) by 337 days.

(21) Appl. No.: 16/068,963

(22) PCT Filed: Oct. 19, 2016

(86) PCT No.: PCT/EP2016/075060
§ 371 (c)(1),
(2) Date: Jul. 10, 2018

(87) PCT Pub. No.: WO2017/067970
PCT Pub. Date: Apr. 27, 2017

(65) Prior Publication Data

US 2019/0025288 A1 Jan. 24, 2019

(30) Foreign Application Priority Data

Oct. 22, 2015 (EP) .................................... 15191075
Oct. 22, 2015 (EP) .................................... 15191076
Nov. 18, 2015 (EP) .................................... 15195198
Nov. 18, 2015 (EP) .................................... 15195202
Nov. 18, 2015 (WO) ................ PCT/EP2015/076967
Nov. 18, 2015 (WO) ................ PCT/EP2015/076971
Dec. 16, 2015 (WO) ................ PCT/EP2015/079915
Mar. 23, 2016 (EP) .................................... 16161820
Jun. 17, 2016 (EP) .................................... 16174974

(51) Int. Cl.
*G01N 33/50* (2006.01)
*C12N 15/11* (2006.01)
*C12N 5/071* (2010.01)

(52) U.S. Cl.
CPC ......... *G01N 33/5014* (2013.01); *C12N 5/067* (2013.01); *C12N 15/111* (2013.01); *C12N 2310/3231* (2013.01); *C12N 2320/10* (2013.01); *C12N 2320/53* (2013.01)

(58) Field of Classification Search
CPC .................................................. G01N 33/5014
USPC ........................................................... 506/10
See application file for complete search history.

(56) References Cited

U.S. PATENT DOCUMENTS 5,994,517 A 11/1999 Ts'o et al.
2007/0015147 A1* 1/2007 Mendrick .......... G01N 33/5014 435/6.16
2009/0220561 A1* 9/2009 Jin .................... A61M 37/0092 424/423
2010/0249219 A1 9/2010 Hedtjarn et al.

FOREIGN PATENT DOCUMENTS

| | | |
|---|---|---|
| EP | 1984381 | 10/2008 |
| WO | WO 01/23613 | 4/2001 |
| WO | WO 2004/046160 | 6/2004 |
| WO | WO 2005/061710 | 7/2005 |
| WO | WO 2006/050732 | 5/2006 |
| WO | WO 2007/031091 | 3/2007 |
| WO | WO 2007/112754 | 10/2007 |
| WO | WO 2007/134181 | 11/2007 |
| WO | WO 2007/146511 | 12/2007 |
| WO | WO 2008/113832 | 9/2008 |
| WO | WO 2008/131807 | 11/2008 |
| WO | WO 2008/150729 | 12/2008 |
| WO | WO 2008/154401 | 12/2008 |
| WO | WO 2009/006478 | 1/2009 |
| WO | WO 2009/043353 | 4/2009 |
| WO | WO 2009/067647 | 5/2009 |
| WO | WO 2009/090182 | 7/2009 |
| WO | WO 2009/100320 | 8/2009 |
| WO | WO 2009/124238 | 10/2009 |
| WO | WO 2009/124295 | 10/2009 |
| WO | WO 2009/126933 | 10/2009 |
| WO | WO 2010/036698 | 4/2010 |
| WO | WO 2011/017521 | 2/2011 |
| WO | WO 2011/085102 | 7/2011 |
| WO | WO 2011/115818 | 9/2011 |
| WO | WO 2012/083046 | 6/2012 |
| WO | WO 2012/089352 | 7/2012 |
| WO | WO 2013/154798 | 10/2013 |
| WO | WO 2014/118267 | 8/2014 |

(Continued)

OTHER PUBLICATIONS

Burdick et al., "Sequence motifs associated with hepatotoxicity of locked nucleic acid—modified antisense oligonucleotides," Nucleic Acids Research, Feb. 18, 2014, 42(8):4882-4891.

(Continued)

*Primary Examiner* — Karla A Dines
(74) *Attorney, Agent, or Firm* — Fish & Richardson P.C.

(57) ABSTRACT

The invention relates to methods for predicting the in vivo toxicity of oligonucleotides, such as antisense oligonucleotides using in vitro cell based assays based on gymnotically administering oligonucleotides to primary mammalian hepatocytes and subsequently measuring the levels of toxicity biomarkers such as the release of LDH into the cell culture media and/or intracellular ATP.

16 Claims, 10 Drawing Sheets

Specification includes a Sequence Listing.

(56) References Cited

FOREIGN PATENT DOCUMENTS

| | | |
|---|---|---|
| WO | WO 2014/179445 | 11/2014 |
| WO | WO 2014/179620 | 11/2014 |
| WO | WO 2016/079181 | 5/2016 |
| WO | WO 2016/079183 | 5/2016 |

OTHER PUBLICATIONS

Burel at el., "Hepatotoxicity of high affinity gapmer antisense oligonucleotides is mediated by RNase H1 dependent promiscuous reduction of very long pre-mRNA transcripts," Nucleic Acids Research, Nov. 8, 2015, 44(5):2093-2109.

Deleavey and Damha, "Designing Chemically Modified Oligonucleotides for Targeted Gene Silencing," Chemistry and Biology 2012, 19(8):937-954.

Filipowics and Grosshans, "The liver-specific microRNA miR-122: biology and therapeutic potential," Prog Drug Res., 5 67:221-238.

Fluiter et al., "Filling the gap in LNA antisense oligo gapmers: the effects of unlocked nucleic acid (UNA) and 4'-C-hydroxymethyl-DNA modifications on RNase H recruitment and efficacy of an LNA gapmer," Mol. Biosyst., Aug. 2009, 5(8):838-843.

Freier and Altmann, "The ups and downs of nucleic acid duplex stability: structure-stability studies on chemically-modified DNA:RNA duplexes," Nucl. Acid Res., Nov. 15, 1997, 25(22):4429-4443.

Frieden "The application of locked nucleic acids in the treatment of cancer," Idrugs., Oct. 2009, 9(10):706-711.

Hagedorn et al., "Hepatotoxic potential of therapeutic oligonucleotides can be predicted from their sequence and modification pattern," Nucleic Acid Ther., Oct. 2013, 23(5):302-310.

Hangeland et al., "Cell-type specific and ligand specific enhancement of cellular uptake of oligodeoxynucleoside methylphosphonates covalently linked with a neoglycopeptide, YEE(ah-Ga1NAc)3," Bioconjug Chem. Nov.-Dec. 1995, 6(6):695-701.

Raetz et al., "A phase I study of EZN-3042, a novel survivin messenger ribonucleic acid (mRNA) antagonist, administered in combination with chemotherapy in children with relapsed acute lymphoblastic leukemia (ALL): a report from the therapeutic advances in childhood leukemia and lymphoma (TACL) consortium," J Pediatr Hematol Oncol., Aug. 2014, 36(6):458-463.

Rukov et al., "Dissecting the target specificity of RNase H recruiting oligonucleotides using massively parallel reporter analysis of short RNA motifs," 2015 Nucl. Acids Res., 43(17):8476-8487.

Seth at al., "Synthesis and biophysical evaluation of 2',4'-constrained 2'O-methoxyethyl and 2',4'-constrained 2'O-ethyl nucleic acid analogues," J. Org. Chem., Mar. 5, 2010, 75(5):1569-1581.

Stein et al., "Efficient gene silencing by delivery of locked nucleic acid antisense oligonucleotides, unassisted by transfection reagents," NAR 2010 38(1):e3.

Soifer et al., "Silencing of gene expression by gymnotic delivery of antisense oligonucleotides," Methods Mol Biol., 2012, 815:333-346.

Su et al., "Serum microRNA-122 level correlates with virologic responses to pegylated interferon therapy in chronic hepatitis C," PNAS, May 7, 2013, 110(19):7844-7849.

Swayze et al., "Antisense oligonucleotides containing locked nucleic acid improve potency but cause significant hepatotoxicity in animals," Nucleic Acids Res., Jan. 2007, 35(2):687-700.

Takayama et al., "Efficient generation of functional hepatocytes from human embryonic stem cells and induced pluripotent stem cells by HNF4α transduction," Molecular Therapy,Jan. 2012, 20(1):127-137.

Uhlmann, "Recent advances in the medicinal chemistry of antisense oligonucleotides," Curr. Opinion in Drug Development, Mar. 1, 2000, 3(2):293-213.

Wang et al., "Circulating microRNAs, potential biomarkers for drug-induced liver injury," Proc Natl Acad Sci USA., Mar. 17, 2009, 106(11):4402-4407.

Williams, "Long-term cell culture of adult rat liver epithelial cells," Exp. Cell Res., 1974, 89(1):139-142.

Vester et al., "Chemically modified oligonucleotides with efficient RNase H response," Bioorg. Med. Chem. Lett., Apr. 1, 2008, 18(7):2296-2300.

Sewing et al, "Establishment of a Predictive In Vitro Assay for Assessment of the Hepatotoxic Potential of Oligonucleotide Drugs", PLoS One, 2016, 11(7):e0159431.

* cited by examiner

Figure 7

In vivo toxicity (mouse):

In vitro toxicity (primary mouse hepatocytes):

| Readout | c [µM] | 32 | 33 | 35 | 38 | 39 | 40 | 42 | 44 | 46 | 51 | GR4b | GR4d | SSO3 | SSO12 | NTS | TS2 | 48 | 45 |
|---|---|---|---|---|---|---|---|---|---|---|---|---|---|---|---|---|---|---|---|
| ALT level | | | | | * | | | | | | | | | | | | | | |
| LDH %vehicle | 3 | 102 | 82 | 103 | 99 | 102 | 93 | 95 | 130 | 108 | 87 | 109 | 101 | 107 | 96 | 79 | 82 | 111 | 123 |
| | 10 | 105 | 89 | 99 | 111 | 105 | 100 | 91 | 122 | 111 | 83 | 122 | 115 | 116 | 107 | 72 | 84 | 129 | 130 |
| | 30 | 111 | 92 | 103 | 120 | 109 | 104 | 98 | 117 | 101 | 118 | 140 | 138 | 102 | 106 | 81 | 90 | 148 | 133 |
| ATP %decrease | 3 | 13 | 18 | 3 | 44 | 15 | 19 | 20 | 10 | 18 | 3 | 14 | -18 | 25 | 14 | 15 | 16 | 23 | 32 |
| | 10 | 15 | 20 | 1 | 50 | 16 | 20 | 23 | 17 | 22 | 9 | 28 | -14 | 35 | 22 | 11 | 24 | 39 | 39 |
| | 30 | 18 | 21 | 3 | 49 | 20 | 19 | 25 | 23 | 25 | 15 | 48 | -1 | 36 | 25 | 9 | 21 | 48 | 43 |

No mild toxicity

In vivo toxicity (mouse):

In vitro toxicity (primary mouse hepatocytes):

| Readout | c [µM] | 49 | R2 | SSO1 | SSO27 | 36 | 43 | GR4a | GR4c | 37 | 41 | 47 | 50 | R1 | GR1 | GR2 | GR3 |
|---|---|---|---|---|---|---|---|---|---|---|---|---|---|---|---|---|---|
| ALT level | | | | | | | | | | | | | * | | | | |
| LDH %vehicle | 3 | 127 | 118 | 127 | 142 | 147 | 191 | 166 | 107 | 160 | 199 | 141 | 94 | 142 | 209 | 310 | 292 |
| | 10 | 140 | 139 | 138 | 133 | 163 | 244 | 209 | 133 | 182 | 215 | 200 | 105 | 175 | 220 | 327 | 285 |
| | 30 | 148 | 153 | 159 | 146 | 177 | 271 | 226 | 164 | 207 | 229 | 241 | 109 | 198 | 243 | 329 | 285 |
| ATP %decrease | 3 | 54 | 21 | 34 | 28 | 16 | 84 | 74 | 36 | 44 | 70 | 58 | 15 | 41 | 59 | 98 | 98 |
| | 10 | 67 | 32 | 46 | 33 | 23 | 91 | 86 | 48 | 56 | 74 | 81 | 18 | 56 | 73 | 100 | 99 |
| | 30 | 71 | 48 | 59 | 43 | 36 | 93 | 92 | 57 | 64 | 83 | 90 | 25 | 76 | 88 | 101 | 100 |

In vivo and in vitro hepatotoxicity

| ALT | <150 | 150-300 | 300-800 | >800 |
|---|---|---|---|---|
| Scale | | | | |
| LDH | <120 | 120-150 | 150-200 | >200 |
| ATP | 0-20 | 20-40 | 40-60 | >60 |

* outlier

| mouse in vivo | SSO | Safe | | | Hepatotoxic | | | |
|---|---|---|---|---|---|---|---|---|
| | | 32 | 33 | 35 | 36 | 37 | 43 | 47 |
| | ALT | 64 U/L | 59 U/L | 67 U/L | 1889 U/L | 2368 U/L | 1890 U/L | ND |

| Readout | c [μM] | 32 | 33 | 35 | 36 | 37 | 43 | 47 |
|---|---|---|---|---|---|---|---|---|
| LDH %vehicle | 10 | 111 | 105 | 104 | 98 | 124 | 120 | 105 |
| | 30 | 113 | 105 | 107 | 106 | 150 | 146 | 107 |
| | 100 | 113 | 108 | 106 | 112 | 169 | 169 | 110 |
| ATP %decrease | 10 | 2 | 10 | 14 | 17 | 44 | 33 | 5 |
| | 30 | 8 | 10 | 20 | 28 | 70 | 67 | 13 |
| | 100 | 15 | 17 | 27 | 38 | 87 | 90 | 26 |

B

| Readout | c [μM] | Survivin | Bcl2 |
|---|---|---|---|
| LDH %vehicle | 3 | 171 | 131 |
| | 10 | 182 | 142 |
| | 30 | 195 | 160 |
| ATP %decrease | 3 | 26 | 28 |
| | 10 | 29 | 38 |
| | 30 | 36 | 48 |

C

| Readout | c [μM] | Survivin | Bcl2 |
|---|---|---|---|
| LDH %vehicle | 30 | 117 | 118 |
| | 100 | 136 | 120 |
| | 300 | 158 | 139 |
| ATP %decrease | 30 | 31 | 29 |
| | 100 | 38 | 40 |
| | 300 | 39 | 48 |

| ALT | <150 | 150-300 | 300-800 | >800 |
|---|---|---|---|---|
| Scale | | | | |
| LDH | <120 | 120-150 | 150-200 | >200 |
| ATP | 0-20 | 20-40 | 40-60 | >60 |

Figure 10

| LNAs | | Compound | | | | | control LNAs | |
|---|---|---|---|---|---|---|---|---|
| Readout | c [µM] | #56 | #57 | #58 | #60 | #59 | - | + |
| LDH % control | 1 | 160 | 173 | 91 | 85 | 174 | | |
| | 3 | 184 | 198 | 93 | 98 | 217 | | |
| | 10 | 210 | 223 | 112 | 112 | 256 | | |
| | 30 | 246 | 225 | 116 | 112 | 257 | 114 | 256 |
| ATP % control | 1 | 71 | 59 | 87 | 81 | 64 | | |
| | 3 | 59 | 45 | 83 | 71 | 53 | | |
| | 10 | 50 | 40 | 78 | 69 | 44 | | |
| | 30 | 43 | 32 | 75 | 64 | 37 | 101 | 28 |

Severity no tox tox

IN VITRO TOXICITY SCREENING ASSAY

FIELD OF INVENTION

The invention relates to methods for predicting the in vivo toxicity of oligonucleotides, such as antisense oligonucleotides using in vitro cell based assays. The invention relates to methods for predicting the in vivo toxicity of oligonucleotides, such as antisense oligonucleotides using in vitro cell based assays based on gymnotically administering oligonucleotides to primary mammalian hepatocytes or hepatocytes derived from induced pluripotent stem cells (iPS cells), and subsequently measuring the levels of toxicity biomarkers such as the release of LDH into the cell culture media and/or intracellular ATP.

BACKGROUND

The promise of antisense oligonucleotides as therapeutic agents has long been recognised, and there are presently considerable interest in developing oligonucleotides to address a large number of diverse medical indications, many of which have been considered undruggable by other means.

The discovery and pre-clinical and clinical development of oligonucleotide drug candidates is a complex process with considerable focus on identification of the unique combinations of sequence, chemistries and designs which can lead to an optimised molecule with desirable drug like properties.

One of the major issues in identification of such optimised drug candidates is the event of unpredictable toxicity. When evaluated in vivo, typically a sub-set of antisense compounds will elicit a toxicity phenotype, such as liver toxicity (hepatotoxicity). Over the past few years it has been recognised that in vitro toxicity assays are not predictive of in vivo toxicity (Burdick et al., Nucleic Acids Research, Feb. 18, 2014). For many years, this has meant that preclinical toxicity screening has been performed in vivo, typically in rodents, such as mice and rats. There is however a desire to reduce the use of animals in drug discovery and development, as well as a concern that animal model species may not be predictive of human toxicities.

Given the previous failure of in vitro cell based assays, pharmaceutical companies have invested in sophisticated bioinformatics algorithms to predict in vivo toxicity. Such approaches are primarily based on the correlation of cryptic oligonucleotide sequence motifs with in vivo datasets, to generate in silico assays (see Hagedorn et al., 2013, Nucleic Acid Therapeutics 23(5) 302-310, and Burdick et al., Nucleic Acids Research, Feb. 18, 2014). Such in silico methods are remarkably effective in predicting in vivo toxicity in mice (for example the algorithm used in Hagedorn et al., accurately predicted about 80% on in vivo toxicities, but they require a substantial data set from in vivo experiments and are inherently limited to the specific chemistry and designs used to generate the in vivo dataset. Recently, Burel et al., has reported that hepatotoxicity of antisense oligonucleotide gapmers is mediated by RNaseH1 dependent promiscuous reduction of very long pre-mRNA transcripts in the liver, raising the possibility that expression profiling or in silico bioinformatics analysis of potential off-targets may be a useful tool in predicting in vivo toxicities. In silico expression profiling can identify potential "off-targets", but it is not generally predictive of actual off-target activity in vivo, and expression profiling of libraries of oligonucleotides is a resource demanding activity. Furthermore, if such methods are found to be predictive, they are again inherently limited to RNaseH gapmer designs. It is also well recognised that toxicity may be hybridisation independent, and as such transcript profiling is unlikely to identify toxicities which are not related to mRNA hybridisation and RNaseH cleavage.

Swayze et al., Nucleic Acids Res. 2007 January; 35(2): 687-700, discloses that some but not all LNA oligonucleotides are hepatotoxic, and uses a transfection based caspase assay in A549 cells.

There is therefore a general need to provide predictive assays for in vivo and clinical toxicity of oligonucleotides.

SUMMARY OF THE INVENTION

The invention also provides in vitro toxicity assays which have been found to be predictive for in vivo toxicity of oligonucleotides, such as antisense oligonucleotides. In an important aspect of the invention, primary mammalian hepatocytes are used in an in vitro toxicity assay for assessing or predicting the toxicity potential of oligonucleotides. The present inventors have also identified certain molecular markers of toxicity, which when used in the primary mammalian hepatocyte assay have been found to be predictive of the in vivo toxicity profile. By correlating a panel of compounds whose toxicity profile has been characterized from human clinical trials, the inventors have also shown that not only are the methods of present invention predictive of in vivo toxicity in model species, such as mouse or rat, but they are also predictive of the toxicity in humans.

The present invention therefore provides an effective in vitro assay for assessing or predicting in vivo toxicity, irrespective of the sequence, chemistry, design, off-targets of the oligonucleotide compounds being tested. For the first time, the present invention provides a robust empirical assay for in vitro determination of in vivo toxicity potential of oligonucleotides, such as antisense oligonucleotides.

The invention provides for an in vitro screen (an assay) for in vivo toxicity (or in vivo toxicity potential) which may be used to select oligonucleotide compounds which are, or are predicted to be, or have the potential to be, suitable for in vivo administration without adverse toxicity, such as without adverse hepatotoxicity. The invention provides for a method for predicting the in vivo toxicity (such as hepatotoxicity) of an oligonucleotide in a mammal, said method comprising the steps of:

a. administering the oligonucleotide to a population of primary mammalian hepatocyte cells (or a population of hepatocytes derived from induced pluripotent stem cells (iPS cells)) in vitro in a cell culture media;
b. and culturing the cells in vitro in the cell culture media for a period of time;
c. and subsequently measuring the amount of at least one biomarker of toxicity, such as hepatotoxicity;

The invention provides for a method for determining the likely in vivo toxicity (such as hepatotoxicity) of an oligonucleotide in a mammal, said method comprising the steps of:

a. administering the oligonucleotide to a population of primary mammalian hepatocyte cells (or a population of hepatocytes derived from induced pluripotent stem cells (iPS cells)) in vitro in a cell culture media;
b. and culturing the cells in vitro in the cell culture media for a period of time;
c. and subsequently measuring the amount of at least one biomarker of toxicity, such as hepatotoxicity.

The invention provides for a method for selecting one or more oligonucleotides (e.g. for in vivo administration), from a library of oligonucleotides, said method comprising the steps of a. Obtaining a library of oligonucleotides
b. administering each oligonucleotide separately to a population of primary mammalian hepatocyte cells(or a population of hepatocytes derived from induced pluripotent stem cells (iPS cells)) in vitro in a cell culture media;
c. culturing the cells in vitro in the cell culture media for a period of time;
d. subsequently measuring the amount of at least one biomarker of toxicity, such as hepatotoxicity, from each population of mammalian hepatocyte cells
e. and selecting one or more oligonucleotides which did not result in an alteration of the at least one biomarker of toxicity.

Optionally the method may further comprise the step of administering the selected oligonucleotide in vivo to a mammal.

Typically, the step of administration of the oligonucleotide to a population of primary mammalian hepatocyte cells (or a population of hepatocytes derived from induced pluripotent stem cells (iPS cells)) in vitro in a cell culture media occurs in the absence of a transfection agent, i.e. by the process referred to as gymnosis (also known as natural uptake).

Suitably, in the method of the invention the level or amount of the at least one biomarker may be compared to control data (or reference value(s)) to determine the level of increase or decrease of the at least one biomarker due to the administration of the oligonucleotide (i.e. an alteration of the at least one biomarker of toxicity, such as hepatotoxicity).

In some embodiments, the at least one biomarker for toxicity, such as hepatotoxicity, is the amount (or level) of lactate dehydrogenase (LDH) released into the cell culture media, or measuring the level of cellular ATP levels. An increase in lactate dehydrogenase in the cell culture media, or a decrease in (intra)cellular ATP levels is indicative of an oligonucleotide which is or is predicted to be hepatotoxic in vivo in the mammal.

In some embodiments, the at least one biomarker for toxicity, such as hepatotoxicity, is the amount (or level) of one or more hepatocytes expressed microRNA, such as microRNA-122 in the cell culture media. An elevation of hepatocytes expressed microRNA, such as microRNA-122 in the cell culture media is indicative of an oligonucleotide which is or is predicted to be hepatotoxic in vivo in the mammal.

In some embodiments, for example when using co-cultures of primary mammalian hepatocytes and primary mammalian liver non parenchymal cells, at least one biomarker for toxicity, such as hepatotoxicity, is the amount (or level) of one or more cytokines in the cell culture media. An elevation of in the cell culture media is indicative of an oligonucleotide which is or is predicted to be hepatotoxic in vivo in the mammal. Specific cytokines which are useful biomarkers for use in the method of the present invention include Macrophage Inflammatory Protein 1 alpha (MIP1a) and/or Interleukin 1 alpha (IL1a).

In some embodiments, the at least one biomarker for toxicity is the level of intracellular glutathione levels (GSH). A decrease in cellular GSH levels is indicative of an oligonucleotide which is or is predicted to be hepatotoxic in vivo in the mammal.

In some embodiments the at least one biomarker is at least is the amount (or level) of lactate dehydrogenase (LDH) released into the cell culture media, or the level of (intra) cellular ATP levels.

In some embodiments the at least one biomarker is at least is the amount (or level) of lactate dehydrogenase (LDH) released into the cell culture media, and the level of (intra) cellular ATP levels. Using the methods of the invention, both LDH release into the culture media and decreased intracellular ATP have been found to be early (i.e. the signal is detectable at an early time point post gymnotic delivery), non-transient and therefore suited to end-point determination, as well as highly discriminatory biomarkers for in vivo toxicity.

In some embodiments the at least one biomarker is at least is the amount (or level) of lactate dehydrogenase (LDH) released into the cell culture media, and the level of (intra) cellular ATP levels and the level of liver expressed microRNAs such as miR-122 released into the cell culture medium.

In some embodiments the at least one biomarker is at least is the amount (or level) of lactate dehydrogenase (LDH) released into the cell culture media, and the level of (intra) cellular ATP levels and the level of intracellular glutathione levels (GSH).

The invention provides for the use of an in vitro primary hepatocyte assay to determine the (e.g. likely) hepatotoxicity of an oligonucleotide such as a LNA oligonucleotide.

The invention provides for the use of an in vitro hepatocytes assay to determine the (e.g. likely) hepatotoxicity of an oligonucleotide such as a LNA oligonucleotide, wherein the hepatocytes are derived from induced pluripotent stem cells (iPS cells)

The invention is applicable to oligonucleotides in general, such as antisense oligonucleotides, including LNA oligonucleotides (e.g. beta-D-oxy LNA or (S)cET for example), and oligonucleotides comprising 2'-substituted nucleosides, gapmer oligonucleotides, such as the oligonucleotide described herein.

The invention provides a method for predicting the (e.g. likely) in vivo hepatotoxicity of an oligonucleotide, such as a LNA oligonucleotide, said method comprising the steps of administering the oligonucleotide to a population of primary hepatocyte cells (or in vitro, such as a mouse or rat primary hepatocyte cells (which may be obtained by liver perfusion by example), pig (e.g. minipig),dog or non human primate (e.g. cynomolgus monkey), primary hepatocytes cells, or a human primary hepatocyte cell, incubating the cells in the presence of the oligonucleotide, e.g. for a period of between about 1-about 7 days, such as about 1-about 4 days, or about 1-about 3 days, or about 2-about 4 days, such as about 2-about 3 days, and subsequently measuring at least one biomarker of in vitro cellular toxicity, such as those described herein, e.g. by measuring the amount of Lactate dehydrogenase (LDH) released into the culture media, and/or determination of cellular ATP levels. Suitably a reduction in cellular ATP levels is indicative of a hepatotoxic oligonucleotide, and elevation of LDH released into the culture media is indicative of a hepatotoxic oligonucleotide. In some embodiments the primary hepatocytes cells are cryopreserved. In some embodiments the population of hepatocytes derived from induced pluripotent stem cells (iPS cells) are cryopreserved. Hepatocytes derived from induced pluripotent stem cells (iPS cells) are commercially available, for example from Axiogenesis or Cellular Dynamics International (CDI)—e.g. iCell® Hepatocytes 2.0. In some embodiments the hepatocytes derived from induced pluripotent stem cells (iPS cells) are derived from human stem cells.

The invention provides for the use of an in vitro assay to determine the (e.g. likely) hepatotoxicity of an oligonucleotide such as a LNA oligonucleotide.

The invention provides for a method of reducing the toxicity of an oligonucleotide sequence, comprising the steps of:

a. Providing an oligonucleotide (the parent) which has a toxicity phenotype in vivo or in vitro b. Creating a library of oligonucleotide variants (the children), retaining the core nucleobase sequence of the parent gapmer oligonucleotide c. Screening the library created in step b. In the in vitro method of the invention (i.e. in a population of primary mammalian hepatocyte cells (or a population of hepatocytes derived from induced pluripotent stem cells (iPS cells))—e.g. via gymnosis.

d. Identify one or more child oligonucleotides which have a reduced toxicity as compared to the parent oligonucleotide.

This method can be used to screen libraries of oligonucleotides which retain the core nucleobase sequence of the parent, but, for example comprise a range of different designs, e.g. gapmer designs, including mixed wing designs, or different chemical modifications (e.g. different internucleoside linkages, such as stereodefined internucleoside linkages).

The invention provides for a method of reducing the toxicity of a stereo unspecified phosphorothioate oligonucleotide sequence, comprising the steps of:

a. Providing a stereo unspecified phosphorothioate oligonucleotide (the parent) which has a toxicity phenotype in vivo or in vitro b. Creating a library of stereo specified phosphorothioate oligonucleotides (the children), retaining the core nucleobase sequence of the parent gapmer oligonucleotide c. Screening the library created in step b. In the in vitro method of the invention (i.e. in a population of primary mammalian hepatocyte cells—e.g. via gymnosis)

d. Identify one or more stereo specified phosphorothioate oligonucleotides which have a reduced toxicity as compared to the stereo unspecified phosphorothioate oligonucleotide.

The stereo specified phosphorothioate oligonucleotides may be as according to the oligonucleotides as disclosed herein. In some embodiments, the parent oligonucleotide is a gapmer oligonucleotide, such as a LNA gapmer oligonucleotide as disclosed herein. In some embodiments, the library of stereo specified phosphorothioate oligonucleotides comprises of at least 2, such as at least 5 or at least 10 or at least 15 or at least 20 stereospecified phosphorothioate oligonucleotides.

The screening method may further comprise a step of screening the children oligonucleotides for at least one other functional parameter, for example one or more of RNaseH recruitment activity, RNase H cleavage specificity, target specificity, target binding affinity, and/or in vivo or in vitro potency.

The method of the invention may therefore be used to reduce the toxicity associated with the a (e.g. parent) oligonucleotide.

The selected (child) oligonucleotides identified by the screening method are therefore safer effective antisense oligonucleotides.

BRIEF DESCRIPTION OF THE FIGURES

FIG. 7 In vitro prediction of ASO induced hepatotoxicity in primary mouse hepatocytes. Increase in secreted LDH levels and reduction in cellular ATP levels after 3 day treatment of primary mouse hepatocytes with 34 ASOs with different in vivo hepatotoxicity as reported by plasma ALT concentration after sub-chronic treatment. *outliers.

FIG. 8 ASO induced toxicity in cryopreserved human hepatocytes. Changes in secreted LDH and cellular ATP concentrations after 3 day treatment with a tool set of hepatotoxic and non-hepatotoxic Myd 88 ASOs (A) and two ASOs that have been tested in the clinic (B) N=2 independent experiments in triplicates.

FIG. 10 Stereodefined ASOs—In vitro toxicity screening in primary mouse hepatocytes. Changes in LDH levels in the supernatants and intracellular ATP levels of cells treated for 3 days with the respective LNAs. Data are mean values and expressed as % vehicle control (n=4 experiments in triplicates for #56 and n=2 experiments in triplicates for all other LNAs).

DETAILED DESCRIPTION OF THE INVENTION

Prediction of In Vivo Toxicity

Figure 1:
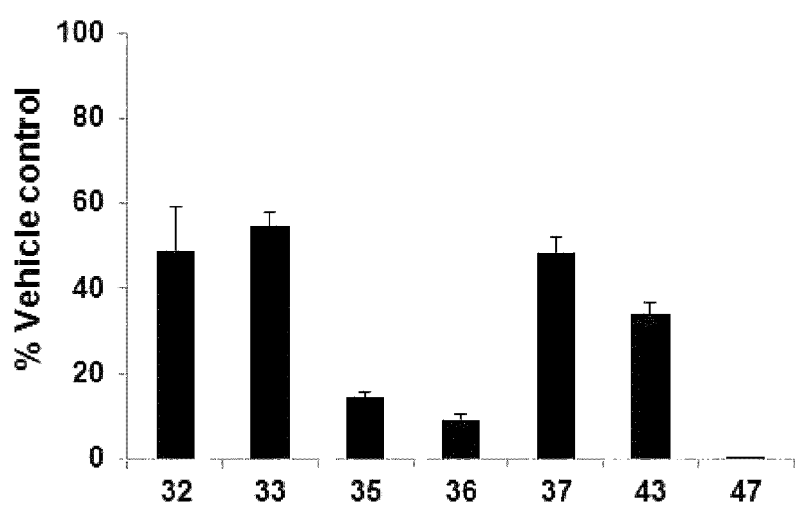
FIG. 1 ASO induced target knock down in primary mouse hepatocytes. Normalized expression of myd88 mRNA after 48 hour treatment of mouse hepatocytes with 30 μM of the respective oligonucleotide. Data are means±StDev.

The methods described herein may be used to predict the in vivo toxicity of an oligonucleotide in a mammal. Toxicity of any compound is typically dependent upon its dose, and as such the methods of the invention may be used to assess a compounds comparative toxicity profile as compared to either a negative control, and oligonucleotides whose toxicity profile is known, or compared to a population (or a library) of other oligonucleotides. In this respect, the prediction of in vivo toxicity may be an assessment of the comparative risk of encountering a toxicity phenotype, such as hepatotoxicity, when the oligonucleotide(s) are administered in vivo in a mammal.

Some ASOs are known to induce acute hepatotoxicity in a dose dependent manner even after a single administration (see e.g. Burel at el NAR November 2015). In some embodiment the toxicity is hepatotoxicity such as acute hepatotoxicity.

The methods of the invention may be used therefore to predict the in vivo toxicity (e.g. hepatotoxicity), or alternatively stated to determine the likely in vivo toxicity profile (e.g. hepatotoxicity), of an oligonucleotide in vivo in a mammal. The methods of the invention may therefore be used to identify oligonucleotides which are not toxic (e.g. not hepatotoxic) in vivo, when used at dosages which are effective in modulating their target, or at therapeutically effective doses. The methods of the present invention therefore allows the selection of oligonucleotides which do not exhibit dose limiting toxicity (e.g. hepatotoxicity) when used in vivo at effective dosages. It will be recognised that it is an advantage to have a wide safely margin when selecting oligonucleotides for in vivo or for therapeutic use, and as such the methods of the invention may be used to identify or select oligonucleotides which do not elicit in vivo toxicity, such as hepatotoxicity, when dosed effectively, or at higher doses, e.g. at up to 2× the effective dose, or up to 3× the effective dose, or up to 5× the effective dose, or up to 10× the effective dose. The methods of the invention may therefore be used to identify oligonucleotides for in vivo use which have a maximum tolerated dose higher (e.g. at least 2×, at least 3×, at least 5×, at least 10×) than the effective dose. In this regard the methods of the invention may be used to select oligonucleotides which have a suitable therapeutic index (TI) for safe therapeutic administration (The therapeutic index may be calculated by the following formula TI=in vivo potency $ED_{50}$/maximum tolerated dose).

Primary Mammalian Hepatocyte Cells

Primary mammalian hepatocyte cells hepatocytes are mammalian liver cells which are obtained directly from a mammalian liver, for example by liver perfusion. For in vitro use, it is typically desirable to use immortalised cells for use in cell culture experiments, as this allows easy storage and experimental reproducibility. However, the process of immortalisation typically involves the selection of cells which have mutated to evade the natural processes of cellular senescence. Primary mammalian hepatocyte cells are not immortalised cells. The present inventors have found that primary hepatocyte cells are particularly useful in in vitro gymnosis assays for assessing or predicting the in vivo toxicity of oligonucleotides.

Examples of liver perfusion methods are provided herein and typically involve the isolation of the liver from the mammal followed by collagenase digestion, which is a two-step process. In the first step, the liver is placed in an isotonic solution, in which calcium is removed to disrupt cell-cell tight junctions by the use of a calcium chelating agent. Next, a solution containing collagenase is added to separate the hepatocytes from the liver stroma. This process creates a suspension of hepatocytes, which can be seeded in multi-well plates and cultured for many days or even weeks.

In some embodiments the population of primary mammalian hepatocyte cells are selected from the group are selected from the group consisting of rodent primary hepatocyte cells, such as mouse, rabbit or rat primary hepatocyte cells; primate primary hepatocyte cells, such as monkey or human primary hepatocyte cells, or pig (e.g. mini pig), dog or non human primate (e.g. cynomolgus monkey) primary hepatocytes cells. Human primary hepatocytes are typically obtained from deceased people and are commercially available. Primary hepatocytes cells may be cryopreserved prior to use in the methods of the invention. Cyropreserved primary hepatocytes are commercially available.

In some embodiments, hepatocytes derived from induced pluripotent stem cells (iPS cells) may be used in place of the primary mammalian hepatocytes in the methods of the invention.

In some embodiments, the mammalian primary hepatocytes cells are a monoculture. In some embodiments the mammalian primary hepatocytes cells are a co-culture comprising both primary mammalian hepatocytes and primary mammalian non parenchymal cells. In some embodiments the co culture comprises a ratio of at least 1:1 hepatocytes/non parenchymal cells, and may in some embodiments comprise a higher proportion of non parenchymal cells, such as a ratio of about 1:2.

When using cultures of (or comprising) primary mammalian hepatocytes (i.e. population of primary hepatocytes), or a population of hepatocytes derived from induced pluripotent stem cells (iPS cells)), the present inventors have identified ATP (intracellular levels), LDH(release into cell culture), and microRNA-122 (release into cell culture) as the most predictive biomarkers, and LDH and/or ATP being particularly useful predictors for in vivo toxicity. Intracellular GDH was also found to be predictive, whereas albumin secretion was generally not predictive.

In some embodiments, the mammalian primary hepatocytes are a co-culture of primary mammalian hepatocytes and primary mammalian liver non-parenchymal cells. When using a co-culture of hepatocytes and non-parenchymal cells, in addition to ATP, LDH or microRNA-122, cytokine release into the cell culture may also be predictive for in vivo toxicity.

The present inventors have found that the use of intracellular ATP, or extracellular release of LDH in primary mammalian hepatocytes cell cultures are preferred biomarkers, e.g. for both mono-cultures of primary mammalian hepatocytes, and co-cultures of primary mammalian hepatocytes and primary mammalian non-parenchyma cells. Typically the non-parenchymal cells are liver non-parenchymal cells.

The present inventors have found that the use of intracellular ATP, or extracellular release of LDH in a population of hepatocytes derived from induced pluripotent stem cells (iPS cells) are preferred biomarkers. In some embodiments, the biomarkers used in the method of the invention are intracellular ATP, or extracellular release of LDH only.

The present inventors have found that the use of intracellular GSH in primary mammalian hepatocytes cell cultures is also be a useful biomarkers, e.g. for both mono-cultures of primary mammalian hepatocytes, and co-cultures of primary mammalian hepatocytes and primary mammalian non-parenchyma cells (or a population of hepatocytes derived from induced pluripotent stem cells (iPS cells)).

Typically the non-parenchymal cells are liver non-parenchymal cells.

The Mammal

The mammal referred to in the method of the invention may refer to the source of the primary mammalian hepatocyte cells or the mammal for which the in vivo toxicity is being predicted. Typically cells from rodent species such as mouse, rat or rabbit are used for testing the toxicity of oligonucleotides, but in some embodiments other mammalian species may be used, such as pig (e.g. minipig) dog or non-human primate (e.g. monkey, such as cynomolgus monkey), or a human.

The method of the invention may be used to determine the likely toxicity in vivo of the oligonucleotide(s) in model species such as rodent species such as mouse, rat or rabbit, or pig (e.g. minipig) or dog, or primates, such as monkeys (e.g. cynomolgus monkey), or may be used to determine the likely toxicity in vivo of the oligonucleotide(s) in humans. The inventors have found that the use of rodent primary hepatocytes or human primary hepatocytes are predictive of the toxicity profile seen in vivo on rodent studies as well as in human clinical trials.

Administering the Oligonucleotide—Gymnotic Delivery (Gymnosis)

The oligonucleotide is administered to the population of primary hepatocyte cells in vitro in the absence of a transfection agent. Uptake of the oligonucleotide into the primary hepatocyte cells occurs through the process known as gymnosis (also known as naked delivery, see Stein et al., NAR 2010 38(1) e3 or Soifer et al., Methods Mol Biol 2012, 815: 333-46)). Since its discovery over 5 years ago, gymontic delivery has become a standard tool used in oligonucleotide research, and is a well-established term used in the art. Typically, gymnotic delivery of oligonucleotides utilises a concentration of oligonucleotide of between about 1 μM and about 1000 μM, such as between about 5 μM and about 100 μM, such as between about 10 μM and about 50 μM, such as between about 20 μM and 40 μM such as about 25-35 μM. Suitably oligonucleotides may be administered to the cell culture, e.g. in PBS, to achieve a final concentration of 1-100 μM, such as 5-50 μM, such as 10 or 30 μM.

Gymnotic delivery requires a period of time between administering the oligonucleotide and measuring the biological effect of the oligonucleotide. Typically, for gymnotic delivery this period is at least 7-14 days in length. The present inventors have identified that in the methods of the invention a shorter culturing step may be used for example about 1-about 7 days, such as about 1-about 4 days, or about 1-about 3 days, or about 2-about 4 days, such as about 2-about 3 days such as about 2, about 3, about 4, about 5, about 6, or about 7 days in length. In some embodiments, the culturing step is about 2 days, or about 3 days or about 4 days. Cell culture of mammalian cells is typically performed at or about 37° C., and may further comprise exogenous $CO_2$, such kept in an atmosphere of or about 5% $CO_2$. One of the advantages of the present invention is the early read out of predictive toxicity biomarkers, relatively shortly after the initiation of the culturing period, and that the biomarkers used provide a reliable signal. In this respect, whereas caspase have been used extensively in the art to determine in vitro toxicity (by using transfection (e.g. See Swayze et al, Nucleic Acids Res. 2007 January; 35(2): 687-700), caspase gives a relatively transient signal which is not suited to end-point analysis and is generally not suited to assays based upon end point analysis after gymnotic delivery of the oligonucleotide.

The term about, as used herein is used to represent the specific integer value indicated, as well as a variance margin of +/− 10% about that specifically disclosed integer value.

Measuring the Amount of at Least One Biomarker, e.g. LDH and ATP Levels:

In some embodiments, the at least one biomarker for toxicity, such as hepatotoxicity, is the amount (or level) of lactate dehydrogenase (LDH) released into the cell culture media, or measuring the level of cellular ATP levels. An increase in lactate dehydrogenase in the cell culture media, or a decrease in cellular ATP levels is indicative of an oligonucleotide which is or is predicted to be hepatotoxic in vivo in the mammal.

The present inventors have found that when using primary mammalian hepatocytes in vitro to assess the toxic (e.g. hepatotoxic) potential of oligonucleotides, the release of the enzyme lactate dehydrogenase (LDH) and/or the intracellular ATP levels are particularly effective in predicting the toxic potential in vivo.

In the methods of the invention the measurement of the levels of at least one biomarker, such as extracellular LDH or intracellular ATP, may be compared to a reference value or reference value(s) which are also referred to as control data herein.

The reference values may be obtained from control experiments using the primary hepatocytes or hepatocytes derived from induced pluripotent stem cells (iPS cells) as used in the method of the invention.

In some embodiments, an increase in lactate dehydrogenase in the cell culture media, or a decrease in cellular ATP levels, is compared to a reference value obtained from a population of (primary) hepatocyte cells which have either been treated with an oligonucleotide characterised as not toxic in vivo in the mammal, or untreated cells.

In some embodiments, an increase in lactate dehydrogenase in the cell culture media, and/or a decrease in cellular ATP levels is indicative of an oligonucleotide which is predicted to be hepatotoxic in vivo in the mammal.

In some embodiments, an decrease in cellular GSH levels, is compared to a reference value obtained from a population of (primary) hepatocyte cells which have either been treated with an oligonucleotide characterised as not toxic in vivo in the mammal, or untreated cells.

In some embodiments, the control data (reference value (s)) is obtained from a population of (primary) hepatocyte cells which have either been treated with an oligonucleotide characterised as not toxic in vivo in the mammal, or untreated cells.

Suitably, in some preferred embodiments the method of the invention the level or amount of LDH present in the culture media and/or the intracellular ATP level may be measured, and optionally compared to control data (also referred to as reference value) to determine the level of increase or decrease of the at least one biomarker due to the administration of the oligonucleotide. In some embodiments, the oligonucleotides identified by the method of the invention the level of LDH present in the culture media is at least 20% higher as compared to the reference value and/or the level of cellular ATP is at least 20% lower that the reference value. Typically the reference value is obtained from a control sample using a non-toxic reference oligonucleotide, or a non-oligonucleotide control (see below)—i.e. negative controls. The reference value may, in some embodiments also include values obtained from a known toxic oligonucleotide (positive controls), Control Data/Reference Values An alteration of the at least one biomarker of toxicity may be determined by comparing to control or reference data, e.g. from a negative control (e.g. a known non-toxic oligonucleotide or a no oligonucleotide control), and in some embodiments, the alteration in the at least one biomarker is determined by an alteration of +/− (depending on the biomarker used) at least 10%, such as at least 20%, such as at least 30%, such as at least 40%, such as at least 50%, such as at least 60%.

As is illustrated in the examples, the present inventors have found that a decrease of cellular ATP by at least 20%, such at least about 40%, such as at least about 60%, as compared to a negative control (or reference data obtained therefrom) is indicative of an enhanced propensity to trigger hepatotoxicity in vivo.

As is illustrated in the examples, the present inventors have found that an elevation of LDH present in the media by at least ×1.2, such as at least ×1.5, such as at least ×2, as compared to a negative control (or reference data obtained therefrom), is indicative of an enhanced propensity to trigger hepatotoxicity in vivo (e.g. as found using the cell culture conditions disclosed herein). It should however, be recognised that the actual level of increase/decrease of the biomarker will depend on many factors including the density of primary hepatocyte cells used, the concentration of oligonucleotide used, and the length of time of incubation of the oligonucleotides.

The control data (reference value(s)) may be data obtained from oligonucleotides of known in vivo toxicity profile (e.g. positive and negative oligonucleotide controls), and/or may be from no oligonucleotide controls. In some embodiments, the method of the invention may therefore further comprise the method steps of the invention using the administration of one or more oligonucleotides with a known toxicity (e.g. hepatotoxicity) profile, such as a positive control oligonucleotide which is known to elicit hepatotoxicity and/or a negative control oligonucleotide which is known not to elicit hepatotoxicity, and a comparison of the level of the at least one biomarker from the administration of the oligonucleotide(s) with the levels obtained from the positive and/or negative controls. In addition or alternatively, the control data may be determined by comparing a library of oligonucleotides using the method of the invention, either in series or in parallel, and comparing the level of at least one biomarker of the oligonucleotide with that of each member of the library of oligonucleotides. Such a method allows for the selection of comparatively less toxic (such as hepatotoxic) oligonucleotides. In some embodiments, the control data may be or may include control data which is from a sample of primary mammalian hepatocyte cells which have not been administered an oligonucleotide (no oligonucleotide control). Such a sample may be obtained immediately prior to the administration step, or may be obtained from a sample which is treated identically to the "test" oligonucleotide(s), other than the administration of the oligonucleotide step.

Liver expressed MicroRNA-122

In some embodiments, the at least one biomarker for toxicity, such as hepatotoxicity, is the amount (or level) of one or more hepatocyte expressed microRNA, such as microRNA-122 in the cell culture media. An elevation of hepatocytes expressed microRNA, such as microRNA-122 in the cell culture media is indicative of an oligonucleotide which is or is predicted to be hepatotoxic in vivo in the mammal.

MicroRNA-122 is a liver expressed microRNA which is conserved through mammalian (and vertebrate) species. The mature microRNA has the sequence:

```
(e.g. hsa-miR-122)
5' uggagugugacaaugguguuug 3'.
or

(e.g. hsa-miR-122a)
5' uggagugugacaaugguguuugu 3'.
```

Serum microRNA-122 levels have been correlated with drug-, alcohol-, hepatitis B virus-, and HCV-related liver diseases and HCC (see e.g. Su et al., PNAS 2013 110 7844-7849).

(Determination of) Hepatotoxicity

Hepatotoxicity may be determined in vivo by assessing the elevation of liver toxicity biomarkers in the serum of a mammal: Liver toxicity biomarkers include serum transaminases, such as aspartate transaminase (AST) and alanine transaminase (ALT) which are routinely used to assess in vivo hepatotoxicity of oligonucleotides. Typically hepatotoxicity is considered to be seen when the levels of ALT or AST are above three times the upper limit of normal.

For example, in vivo oligonucleotide hepatotoxicity may be determined using a model mouse system, see for example EP 1 984 381.

Screening Library of Variants to Identify Child Oligonucleotides with a Predicted Reduced Toxicity Profile In Vivo:

The invention provides for a method for selecting one or more oligonucleotides suitable for in vivo administration to a mammal, from a library of oligonucleotides, said method comprising the steps of:

a. Obtaining a library of oligonucleotides
b. Administer each member of the library of oligonucleotides to a population of primary mammalian hepatocyte cells in vitro via gymnosis;
c. and culturing the cells in vitro for a period of time;
d. measuring the amount of at least one biomarker of toxicity, such as hepatotoxicity for each oligonucleotide
e. selecting one or more oligonucleotides which is or is predicted to be not toxic e.g. hepatotoxic in vivo in the mammal.

and optionally administering the selected oligonucleotides in vivo to the mammal.

In some embodiments, the library of oligonucleotides is a library of oligonucleotides which have different nucleobase sequences, for example they may be a library of oligonucleotides which are designed across a target sequence (e.g. a mRNA), for example a library of oligonucleotides generated by a mRNA gene-walk.

In some embodiments, library of oligonucleotides is a library of oligonucleotide variants (child oligonucleotides) of a parent oligonucleotide, wherein the parent oligonucleotide is toxic, such as hepatotoxic, and wherein step c. identifies one or oligonucleotide variants which are less toxic than the parent oligonucleotide; wherein the oligonucleotide variants retaining the core nucleobase sequence of the parent oligonucleotide.

In some embodiments, the oligonucleotide variants differ from the parent oligonucleotide by the presence of one or more stereodefined phosphorothioate internucleoside linkages.

In some embodiments, the oligonucleotide is an antisense oligonucleotide, such as a gapmer oligonucleotide.

In some embodiments, the oligonucleotide is an LNA oligonucleotide.

In some embodiments, the library of oligonucleotide variants comprises a population of child oligonucleotides which differ by virtue of the design of nucleoside modifications.

In some embodiments, the library of child oligonucleotides are or comprise a population of child oligonucleotides with different gapmer designs, optionally including different mixed wing gapmer designs and/or gap-breaker designs.

Stereodefined Oligonucleotides The method of the invention may be used to identify stereodefined oligonucleotides with reduced in vivo toxicity (such as hepatotoxicity).

In some embodiments the oligonucleotide is 10-20 nucleotides in length, such as 10, 11, 12, 13, 14, 15, 16, 17, 18, 19, 20 nucleotides. In some embodiments the parent and child oligonucleotide is an LNA oligomer. In some embodiments, the LNA oligomer comprises at least one stereoselective phosphorothioate linkage between a LNA nucleoside and a subsequent (3') nucleoside. In some embodiments, the LNA oligomer comprises at least one stereodefined phosphorothioate nucleotide pair wherein the internucleoside linkage between the nucleosides of the stereodefined phosphorothioate nucleotide pair is either in the Rp configuration or in the Rs configuration, and wherein at least one of the nucleosides of the nucleotide pair is a LNA nucleotide. In some embodiments, the other nucleotide of the nucleotide pair is other than DNA, such as nucleoside analogue, such as a further LNA nucleoside or a 2' substituted nucleoside.

In some embodiments, the oligomer is a stereodefined (stereoselective) phosphorothioate LNA oligonucleotide, comprising at least one stereoselective phosphorothioate linkage between a LNA nucleoside and a subsequent (3') nucleoside. Such an LNA oligonucleotide may for example be a LNA gapmer as described herein.

In some embodiment the oligonucleotide comprising a central region (Y') of at least 5 or more contiguous nucleosides, and a 5' wing region (X') comprising of 1-6 LNA nucleosides and a 3' wing region (Z') comprising of LNA 1-6 nucleosides, wherein at least one of the internucleoside linkages of central region are stereodefined, and wherein the central region comprises both Rp and Sp internucleoside linkages.

The invention therefore provides for a method of reducing the toxicity of an antisense oligonucleotide sequence (parent oligonucleotide), comprising the steps of a. Creating a library of stereodefined oligonucleotide variants (child oligonucleotides), retaining the core nucleobase sequence of the parent oligonucleotide.
b. Screening the library created in step a. in a primary mammalian hepatocyte cell (as per the method of the invention as described herein—e.g. via gymnosis)
c. Identify one or more stereodefined variants present in the library which has a reduced toxicity in the cell as compared to the parent oligonucleotide.

wherein, optionally the method is repeated (reiterative screening), for example so that the one or more stereodefined variants identified by the method is used as a parent oligonucleotide in the next round of the screening method. The term stereodefined is interchangeable with the term stereospecified herein.

The invention provides for a method of reducing the toxicity of a phosphorothioate oligonucleotide (parent) sequence, comprising the steps of:

a. Providing a stereo unundefined phosphorothioate oligonucleotide (the parent) which has a toxicity phenotype in vivo or in vitro
b. Creating a library of stereodefined phosphorothioate oligonucleotides (the children), retaining the core nucleobase sequence of the parent gapmer oligonucleotide
c. Screening the library created in step b. in a primary mammalian hepatocyte cell (as per the method of the invention as described herein—e.g. via gymnosis)
d. Identify one or more stereodefined phosphorothioate oligonucleotides which have a reduced toxicity as compared to the stereo undefined phosphorothioate oligonucleotide In some embodiments, the method of the invention may be used reiteratively.

The methods of the invention may further comprise an additional subsequent step of manufacturing the one or more stereodefined phosphorothioate oligonucleotides which have a reduced toxicity. In some embodiments, the subsequent manufacture is in a scale of more than 1 g, such as more than 10 g. In some embodiments, the synthesis of the oligonucleotides for in vivo or in vitro screening steps (b) is performed at a scale of less than 1 g, such as less than 0.5 g, such as less than 0.1 g.

The child oligonucleotides (i.e. members of the library of step b) or the reduced toxicity child oligonucleotides identified by the method, are stereodefined variants of the parent oligonucleotide, i.e. they comprise of at least one stereodefined phosphorothioate internucleoside linkage which differs from parent.

In the method of the invention, each member of the library created in step b) comprises at least one stereodefined phosphorothioate internucleoside linkage which differs from parent.

In some embodiments, the method further comprises the step of determining the in vitro or in vivo potency of either the library of stereodefined oligonucleotide variants, or of the one or more stereodefined compounds present in the library identified in step c) or d).

In some embodiments, the method of the invention provides for a stereodefined phosphorothioate LNA oligonucleotide, comprising at least one stereoselective phosphorothioate linkage between a LNA nucleoside and a subsequent (3') nucleoside. Such an LNA oligonucleotide may for example be an LNA gapmer as described herein. The term stereodefined is used unchangeably with stereospecified herein). A stereodefined phosphorothioate linkage may also be referred to as a stereoselective or stereospecific phosphorothioate linkage.

In some embodiments the oligonucleotide of the invention is 10-20 nucleotides in length, such as 10-16 nucleotides in length.

In some embodiments, the non-stereodefined phosphorothioate oligonucleotide/stereodefined oligonucleotide may be a gapmer, such as a LNA-gapmer. For the comparison of toxicity, the stereodefined phosphorothioate oligonucleotide retains the pattern of modified and unmodified nucleosides present in the parent oligonucleotide.

(also referred to as variants of child oligonucleotides) which have a reduced in vivo toxicity The invention provides for the use of an in vitro primary hepatocyte gymnosis assay to determine the (e.g. likely) hepatotoxicity of an oligonucleotide such as an antisense oligonucleotide such as an LNA oligonucleotide.

The invention provides a method for predicting the (e.g. likely) in vivo hepatotoxicity of an oligonucleotide, such as a LNA oligonucleotide, said method comprising the steps of administering the oligonucleotide to a population of primary hepatocyte cells in vitro via gymnosis, incubating the cells in the presence of the oligonucleotide, e.g. for a period of between 1-7 days, such as 2-4 days, such as 3 days, and subsequently measuring at least one biomarker of toxicity, such as those described herein, e.g. by measuring the amount of Lactate dehydrogenase (LDH) released into the culture media, and/or determination of cellular ATP levels. Suitably a reduction in cellular ATP levels is indicative of a hepatotoxic oligonucleotide, and elevation of LDH released into the culture media is indicative of a hepatotoxic oligonucleotide.

The invention provides for the use of an in vitro assay to determine the (e.g. likely) hepatotoxicity of an oligonucleotide such as a LNA oligonucleotide.

It will be recognised that, in some embodiments, the methods for predicting (or determining) the in vivo toxicity (e.g. hepatotoxicity), may be used to identified stereodefined variants of a parent oligonucleotide which has reduced in vitro or in vivo toxicity.

Parent Oligonucleotide

In some embodiments, the parent oligonucleotide may be a non-stereodefined phosphorothioate oligonucleotide, i.e. an oligonucleotide which comprises a mixture of individual molecules where the chirality of the phosphorothioate linkages are not defined, for example a racemic mixture. In other words, in some embodiments, the parent oligonucleotide may have only stereo unspecified phosphorothioate internucleoside linkages (i.e. a stereo-unspecified oligonucleotide).

In some embodiments the parent oligonucleotide comprises non-stereodefined phosphorothioate internucleoside linkages. In some embodiments, all of the internucleoside linkages present in the parent oligonucleotide are non-stereodefined internucleoside linkages, such as non-stereodefined internucleoside phosphorothioate linkages.

In some embodiments, the parent oligonucleotide may comprise one or more stereodefined phosphorothioate internucleoside linkages. In some embodiments, all of the phosphorothioate internucleoside linkages of the parent oligonucleotide are stereodefined phosphorothioate internucleoside linkages. In some embodiments, the parent oligonucleotide is identified by an earlier reiteration of the method of the invention.

Library of Variants

The method of the invention involves the step of creating a library of variants of the parent oligonucleotide, wherein the variants have at least one stereodefined phosphorothioate internucleoside linkage which differs from the parent oligonucleotide. Suitably, each member of the library of variants has a distinct pattern of defined stereodefined phosphorothioate internucleoside linkages which differ from the parent.

In some embodiments, each member of the library of child oligonucleoitdes (stereodefined defined oligonucleotide variants) comprises at least 2, such as at least 3, such as at least 4 stereodefined phosphorothioate linkages, wherein the remaining linkages may optionally be non-stereodefined defined phosphorothioate linkages. Suitably, the said at least 2, at least 3 or at least 4 stereopsecified phosphorothioate linkages present in the child oligonucleotides differ from the parent (e.g. the parent does not comprise stereodefined phosphorothioate internucleoside linkages, or the parent comprises a different stereodefined phosphorothioate linkage, or a different pattern or stereodefined phosphorothioate linkage).

In some embodiments 5%, 10%, 15%, 20%, 25%, 30%, 35%, 40%, 45%, 50%, 55%, 60%, 65%, 70%, 75%, 80%, 85%, 90%, or 95% of the linkages in the (e.g. child) oligomer(s) are stereodefined phosphorothioate linkages. In some embodiments all of the phosphorothioate linkages in the (e.g. child) oligomer(s) are stereodefined phosphorothioate linkages. In some embodiments the all the internucleoside linkages of the (e.g. child) oligomer(s) are stereodefined phosphorothioate linkages. It should be recognised that stereodefined (stereospecificity) refers to the incorporation of a high proportion, i.e. at least 75%, of either the Rp or the Sp internucleoside linkage at a defined internucleoside linkage.

In some embodiments, in step b) of the method of the invention each member of the library of stereodefined oligonucleotide variants may be created by inserting at least one stereodefined phosphorothioate internucleoside linkage into the gap-region of a parent gapmer. Suitably, either the inserted stereodefined phosphorothioate internucleoside linkage differs from the equivalent internucleoside linkage of the parent, or the parent does not comprise a stereodefined internucleoside linkage at the equivalent position.

In some embodiments, each member of the library of stereodefined oligonucleotide variants is created by inserting at least one stereodefined phosphorothioate internucleoside linkage into the gap-region of the gapmer.

In some embodiments, each member of the library of stereodefined oligonucleotide variants is created by inserting at least one stereodefined phosphorothioate internucleoside linkage into one or both wing-regions of the gapmer.

In some embodiments, each member of the library of stereodefined oligonucleotide variants is created by inserting at least one stereodefined phosphorothioate internucleoside linkage into one or both wing-regions of the gapmer and at least one stereodefined phosphorothioate internucleoside linkage into the gap-region of the gapmer.

It will be recognised that in some embodiments, the remaining internucleoside linkages of a child oligonucleotide, such as the remaining internucleoside linkages of the gap region or of the gapmer compound, may be the same as the parent, or may in some embodiments be different to the parent.

In some embodiments, the child oligonucleotides created in step b) comprise 1, 2, 3, 4, 5, 6, 7, 8, 9, 10, 11, 12, 13, 14, 15, 16, 17, 18, 19 or 20 independently stereodefined phosphorothioate internucleoside linkages. In some embodiments, all of the phosphorothioate internucleoside linkages of the child oligonucleotides created in step b) are stereodefined phosphorothioate internucleoside linkages. In some embodiments, all of the internucleoside linkages of the child oligonucleotides created in step b) are stereodefined phosphorothioate internucleoside linkages.

In some embodiments, each member of the library of stereodefined defined oligonucleotide variants comprises at least 2, such as at least 3, such as at least 4 stereodefined phosphorothioate linkages, wherein the remaining linkages may optionally be non-stereodefined defined phosphorothioate linkages.

In some embodiments, all phosphorothioate linkages present in each member of the library of stereodefined defined oligonucleotide variants are stereodefined defined phosphorothioate linkages.

In some embodiments, all internucleoside linkages present in each member of the library of child oligonucleotides, or gapmer region thereof, are stereodefined phosphorothioate linkages.

In some embodiments, each member of the library of stereodefined defined oligonucleotide variants retains the pattern of modified and unmodified nucleosides present in the parent oligonucleotide, such as antisense gapmer oligonucleotide. In some embodiments, the parent and child oligonucleotides share the same pattern of nucleoside modifications, e.g. the (for example) gapmer design of the parent oligonucleotide is retained in the child oligonucleotides, or at least a proportion of the child oligonucleotides. However, it is recognised that the library of variants may comprise child oligonucleotides that, whilst retaining the overall gapmer design of the parent oligonucleotide, may comprise a few, such as 1 or 2 or 3 or 4 nucleosides where the sugar chemistry of the parent has also been varied, for example by use of an alternative nucleoside in the wing e.g. use of an alternative high affinity nucleoside in the wing regions, or a increase or decrease or shift in the gap region.

In some embodiments the parent and child oligonucelotides are LNA gapmer oligonucleotides.

Retaining the Core Nucleobase Sequence

A library of child oligonucleotides comprises 2 or more (e.g. stereodefined phosphorothioate) oligonucleotides which retain the core nucleobase sequence of the parent compound.

In some embodiments, the child oligonucleotides may be the same length as the parent oligonucleotide and retain the same nucleobase sequence. However, it is envisaged that, in some embodiments, the child oligonucleotides may be truncated, such as by the removal of a 5' and/or 3' terminal nucleotide, or may in some embodiments, have an additional nucleotide at the 5' and/or 3' end. Removal of one or more terminal high affinity nucleosides, such as a LNA nucleoside allows for the affinity of the oligonucleotide to the RNA target to be maintained, as the insertion of one or more LNA nucleosides into the gap region will increase the affinity to the RNA target. It is envisaged that, in some embodiments, the library of child oligonucleotides may comprise variants which have different flank regions, some being truncated, some having additional nucleosides, some having a sequence shifted one or two nucleosides (as measured to the RNA target), some with additional high affinity nucleosides in the flanks, so the library is a complex library of stereodefined phosphorothioate oligonucleotides with heterogeneous phosphorothioate internucleoside linkages, thereby allowing for the concurrent selection of child oligonucleotides which have a decreased toxicity as compared to the parent.

The parent and child oligonucleotides share a common core nucleobase sequence. The common core nucleobase sequence is typically at least 10 nucleobases long, such as at least 11, at least 12, at least 13, at least 14, at least 15, or at least 16 nucleobases long, and in some embodiments may be the same nucleobase sequence of the parent oligonucleotide. In some embodiments the parent and (at least a proportion of) the child oligonucleotides have the same nucleobase sequence across the length of the oligonucleotides. It is however envisaged that a proportion of the child oligonucleotides may, in some embodiments, comprise additional 5' or 3' nucleotides, such as an additional 1, 2 or 3 5' or 3' nucleotides. In addition or alternatively in some embodiments, a proportion of the child oligonucleotides may be truncated with regards the parent, e.g. may comprise 1, 2 or 3nt truncation at the 5' or 3' end. In some embodiments, additional nucleobase or truncations of the nucleobase sequence of the (proportion of) child oligonucleotide(s) is a single nucleobase addition or truncation. In some embodiments, the child oligonucleotides, or a proportion thereof, may be shifted by a single nucleobase, or by 2 or 3 nucleobases in comparison to the parent oligonucleotide when aligned to the target sequence (in effect a truncation at one end, and an addition at the other). Additional nucleotides retain complementarity with the target nucleic acid sequence.

Stereodefined Oligonucleotide Embodiments:

Embodiment 1: The invention provides for a method of reducing the toxicity of an antisense oligonucleotide sequence (parent oligonucleotide), comprising the steps of a. Creating a library of stereodefined oligonucleotide variants (child oligonucleotides), retaining the core nucleobase sequence of the parent oligonucleotide,
b. Screening the library created in step a. for their in vitro toxicity in a primary mammalian hepatocyte according to the method of the invention,
c. Identify one or more stereodefined variants present in the library which has a reduced toxicity in the cell as compared to the parent oligonucleotide.

2. The method according to embodiment 1, wherein the parent oligonucleotide is an antisense gapmer oligonucleotide.

3. The method according to embodiment 2, wherein each member of the library of stereodefined oligonucleotide variants is created by inserting at least one stereodefined phosphorothioate internucleoside linkage into the gap-region of the gapmer.

4. The method according to embodiment 2 or 3, wherein each member of the library of stereodefined oligonucleotide variants is created by inserting at least one stereodefined phosphorothioate internucleoside linkage into one or both wing-regions of the gapmer.

5. The method according to embodiment any one of embodiments 1-4, wherein each member of the library of stereodefined defined oligonucleotide variants comprises at least 2, such as at least 3, such as at least 4 stereodefined phosphorothioate linkages, wherein the remaining linkages may optionally be non-stereodefined defined phosphorothioate linkages.

6. The method according to any one of embodiments 1-5, wherein all phosphorothioate linkages present in each member of the library of stereodefined defined oligonucleotide variants are stereodefined defined phosphorothioate linkages.

7. The method according to any one of embodiments 1-6, wherein all internucleoside linkages present in each member of the library of stereodefined defined oligonucleotide variants, or gapmer region thereof, are stereodefined phosphorothioate linkages.

8. The method according to any one of embodiments 1-7, wherein each member of the library of stereodefined defined oligonucleotide variants retains the pattern of modified and unmodified nucleosides present in the parent oligonucleotide, such as antisense gapmer oligonucleotide.

9. The method according to any one of embodiments 1-8, wherein the parent gapmer oligonucleotide is a LNA gapmer.

10. The method according to any one of embodiments 1-9, wherein the method further comprises the step of determining the in vitro or in vivo potency of either the library of stereodefined oligonucleotide variants, or of the one or more stereodefined compounds present in the library identified in step c).

11. The method according to any one of embodiments 1-10 wherein the stereodefined oligonucleotide variant(s) identified in step c. retain at least 25% such as at least 50% of the in vitro (e.g. 1050) or in vivo (e.g. ED50 or EC50) potency of that of the parent.

12. The method according to any one of embodiments 1-11 wherein the stereodefined oligonucleotide variant(s) identified in step c. retain an EC50 value of not larger than 3 to 10 times that of the parent compound.

13. The method according to any one of embodiments 1-12 wherein the parent gapmer oligonucleotide and the members of the library of stereodefined oligonucleotide variants comprise at least one LNA nucleoside selected from the list of beta-D-oxy-LNA and 6'methyl beta-D-oxy LNA nucleosides (e.g. S(cET)).

14. The method according to any one of embodiments 1-13, wherein the parent oligonucleotide is hepatotoxic, and the one or more stereodefined compounds identified in step c) is less hepatotoxic than the parent oligonucleotide.

15. The method according to any one of embodiments 1-14, wherein the library screen performed in step b) comprises screening for hepatotoxicity in vitro or in vivo.

16. The method according to any one of embodiments 1-15, wherein the library screen performed in step b) comprises screening for hepatotoxicity in vitro in primary hepatocytes, such as primary mammalian, such as mouse or rat hepatotocytes.

Primary Hepatocytes Assay Example:

The following embodiments are an example of the cell culture conditions, and should not be considered limiting aspects of the invention: Freshly isolated primary mouse or cryopreserved human (e.g. purchased from Bioreclamation-IVT, Brussels, Belgium) hepatocytes are suspended in WME supplemented with 10% (e.g. fetal calf) serum, penicillin (100 U/ml), streptomycin (0.1 mg/ml) at a density of approx. $5\times10^6$ cells/ml and seeded into collagen-coated 96-well plates (e.g. as purchased from Becton Dickinson AG, Allschwil, Switzerland) at a density of $0.25\times10^5$-$0.25\times10^6$ cells/well (mouse) and $0.4\times10^5$-$0.4\times10^6$ cells/well (human).

Cells are pre-cultured for 3 to 4 hr allowing for attachment to cell culture plates before start of treatment with oligonucleotides. Seeding medium is replaced by 90 μl of serum free WME (comprising antibiotics as before) and 10 μl of oligonucleotide stock solutions in PBS is added to the cell culture and left on the cells for 2 or 3 days at 37° C. and 5% $CO^2$.

In some embodiments, the cell culture medium is WME (Williams' medium E)—See Williams, G. M. and Gunn, J. M. (1974). Exp. Cell Res., 89:139. WME media is commercially available from numerous sources. In some embodiments the cells are cultured at or about 37° C. In some embodiments the cell culture medium comprise exogenous $CO_2$, such as at added in an atmosphere of or about 5% $CO_2$.

In some embodiments the number of primary mammalian cells in the cell culture medium is about $0.25\times10^5$ or about $0.25\times10^6$ mouse cells/well or about $0.4\times10^5$ or about $0.4\times10^6$ human hepatocytes/well. Cells are pre-cultured for 3 to 4 h allowing for attachment to cell culture plates before start of treatment with oligonucleotides. Seeding medium is replaced by 90 μl of serum free WME and 10 μl of oligonucleotide 10× stock solutions in PBS are added to the cell culture and left on the cells for 3 days. In some embodiments, the number of cells per volume of cell culture medium is $0.1\times10^7$-$1\times10^7$ cells per ml, such as $0.25\times10^7$-$0.4\times10^7$ cells per ml.

In some embodiments, the cell culture medium comprises antibiotics, such as penicillin and/or streptomycin, for example penicillin (100 U/ml), streptomycin (0.1 mg/ml).

Definitions

Oligonucleotide

The term "oligonucleotide", also referred to as "oligomer" herein, as used herein is defined as it is generally understood by the skilled person as a molecule comprising two or more covalently linked nucleosides. Such covalently bound nucleosides may also be referred to as nucleic acid molecules or oligomers. Oligonucleotides are commonly made in the laboratory by solid-phase chemical synthesis followed by purification. When referring to a sequence of the oligonucleotide, reference is made to the sequence or order of nucleobase moieties, or modifications thereof, of the covalently linked nucleotides or nucleosides. The oligonucleotide of the invention is man-made, and is chemically synthesized, and is typically purified or isolated. The oligonucleotide of the invention may comprise one or more modified nucleosides or nucleotides.

The oligomer may consists or comprises of a contiguous nucleotide sequence of from 7-30, such as 7-26 or 8-25, such as 9, 10, 11, 12, 13, 14, 15, 16, 17, 18, 19, 20, 21, 22, 23, 24, 25 nucleotides in length, such as 10-20 nucleotides in length. In some embodiments, the length of the LNA oligomer is 10-16 nucleotides, such as 12, 13 or 14 nucleosides. In some embodiments, the oligomers comprise or consist of a contiguous nucleotide sequence of a total of from 10-22, such as 12-18, such as 13-17 or 12-16, such as 13, 14, 15, 16 contiguous nucleotides in length. In some embodiments, the oligomers comprise or consist of a contiguous nucleotide sequence of a total of 10, 11, 12, 13, or 14 contiguous nucleotides in length. In some embodiments, the oligomer according to the invention consists of no more than 22 nucleotides, such as no more than 20 nucleotides, such as no more than 18 nucleotides, such as 15, 16 or 17 nucleotides. In some embodiments the oligomer of the invention comprises less than 20 nucleotides. It should be understood that when a range is given for an oligomer, or contiguous nucleotide sequence length it includes the lower an upper lengths provided in the range, for example from (or between) 10-30, includes both 10 and 30. In some embodiments, the oligomers has a length of less than 20, such as less than 18, such as 16nts or less or 15 or 14 nts or less. LNA oligomers often have a length less than 20. In some embodiments, the oligomers comprise or consist of a contiguous nucleotide sequence of a total of 10, 11, 12, 13, or 14 contiguous nucleotides in length.

In some embodiments, the oligomer according to the invention consists of no more than 22 nucleotides, such as no more than 20 nucleotides, such as no more than 18 nucleotides, such as 15, 16 or 17 nucleotides. In some embodiments the oligomer of the invention comprises less than 20 nucleotides. It should be understood that when a range is given for an oligomer, or contiguous nucleotide sequence length it includes the lower an upper lengths provided in the range, for example from (or between) 10-30, includes both 10 and 30.

The oligonucleotide(s) referred to in the method of the invention may be or comprise an antisense oligonucleotide, or may be another oligonucleotide compound, such as an siRNA, aptamer, or ribozyme. The oligonucleotide(s) are typically for modulating the expression of one or more nucleic acids in a mammal. In some embodiments, such as for siRNAs and antisense oligonucleotides, the oligonucleotide(s) are typically for inhibiting the expression of an RNA in a mammal, such as a mRNA or microRNA, for example. The oligonucleotides may therefore be effective at modulating the expression of one or more nucleic acids in a mammal.

In some embodiments the oligonucleotide is a phosphorothioate oligonucleotide. In some embodiments the oligonucleotide comprises phosphorothioate internucleoside linkages.

In some embodiments the oligonucleotide(s) may be conjugated to non-nucleosidic moieties (conjugate moieties).

In some embodiments the oligonucleotides used or identified in the method of the invention comprise at least one stereodefined phosphorothioate internucleoside linkage.

Antisense Oligonucleotides (ASOs)

The term "Antisense oligonucleotide" as used herein is defined as oligonucleotides capable of modulating expression of a target gene by hybridizing to a target nucleic acid, in particular to a contiguous sequence on a target nucleic acid. The antisense oligonucleotides are not essentially double stranded and are therefore not siRNAs. Preferably, the antisense oligonucleotides of the present invention are single stranded.

In some embodiments, the antisense oligonucleotide(s) are capable of recruiting RNaseH, and may, for example be a gapmer oligonucleotide, such as an LNA gapmer or mixed wing gapmer, or may be a gap-breaker oligonucleotide.

In some embodiments, the antisense oligonucleotide are mixmers. Mixmer oligonucleotides typically comprise alternating regions of high affinity sugar modified nucleosides, such as LNA nucleosides, with short regions of 1-4 or 1-3 DNA nucleosides. Typically a mixmer will comprise at least alternating regions, for example $[LNA]_{1-5}[DNA]_{1-3}[LNA]_{1-4}[DNA]_{1-3}[LNA]_{1-4}[DNA]_{1-3}$.

Various mixmer designs are highly effective, for example when targeting microRNA (antimiRs), microRNA binding sites on mRNAs (Blockmirs) or as splice switching oligomers (ASOs). See for example WO2007/112754 (LNA-AntimiRs™), WO2008/131807 (LNA splice switching oligos).

In some embodiments, the oligonucleotide may be a TINY LNA oligonucleotide of 7-10 nucleotides in length. Such TINY LNAs are disclosed in WO2009/043353, herein incorporated by reference. They are typically use to inhibit microRNAs and microRNA families, and may be full LNA modified (i.e. each nucleoside is a LNA nucleoside). It is also preferred that as with gapmer and mixmer oligonucleotides, the internucleoside linkages comprise phosphorothioate internucleoside linkages, and as with the oligonucleotides referred to herein may be fully phosphorothiolates oligonucleotides.

Antisense oligonucleotides are typically between 7-30 nucleotides in length, such as between 7-10 nucleotides (e.g. TINY LNAs) or 10-14 nucleotides (e.g. shortmers or short gapmers) or 12-20 or 10-22 or 10-24 nucleotides in length.

In some embodiments the antisense oligonucleotides used or identified in the method of the invention comprise at least one stereodefined phosphorothioate internucleoside linkage.

Modified Internucleoside Linkages

Modified internucleoside linkages may, for example, be selected from the group comprising phosphorothioate, diphosphorothioate and boranophosphate. In some embodiments, the modified internucleoside linkages are compatible with the RNaseH recruitment of the oligonucleotide of the invention, for example phosphorothioate, diphosphorothioate or boranophosphate.

In some embodiments the internucleoside linkage comprises sulphur (S), such as a phosphorothioate internucleoside linkage. In some embodiments the oligonucleotides used or identified in the method of the invention comprise at least one stereodefined phosphorothioate internucleoside linkage.

A phosphorothioate internucleoside linkage is particularly useful due to nuclease resistance, beneficial pharmakokinetics and ease of manufacture. In some embodiments at least 50% of the internucleoside linkages in the oligonucleotide, or contiguous nucleotide sequence thereof, are phosphorothioate, such as at least 60%, such as at least 70%, such as at least 80 or such as at least 90% of the internucleoside linkages in the oligonucleotide, or contiguous nucleotide sequence thereof, are phosphorothioate. In some embodiments all of the internucleoside linkages of the oligonucleotide, or contiguous nucleotide sequence thereof, are phosphorothioate.

In some embodiments, the oligonucleotide comprises one or more neutral internucleoside linkage, particularly a internucleoside linkage selected from phosphotriester, methylphosphonate, MMI, amide-3, formacetal or thioformacetal.

Further internucleoside linkages are disclosed in WO2009/124238 (incorporated herein by reference). In an embodiment the internucleoside linkage is selected from linkers disclosed in WO2007/031091 (incorporated herein by reference). Particularly, the internucleoside linkage may be selected from —O—$P(O)_2$—O—, —O—P(O,S)—O—, —O—$P(S)_2$—O—, —S-$P(O)_2$—O—, —S—P(O,S)—O—, —S—$P(S)_2$—O—, —O—$P(O)_2$—S—, —O—P(O,S)—S—, —S—$P(O)_2$—S—, —O—PO(RH)—O—, 0-PO($OCH_3$)-0-, —O—PO(NRH)—O—, —O—PO($OCH_2CH_2S$—R)—O—, —O—PO($BH_3$)—O—, —O—PO(NHRH)—O—, —O—$P(O)_2$—NRH—, —NRH—$P(O)_2$—O—, —NRH—CO—, —NRH—CO—NRH—, and/or the internucleoside linker may be selected form the group consisting of: —O—CO—O—, —O—CO—NRH—, —NRH—CO—$CH_2$—, —O—$CH_2$—CO—NRH—, —O—$CH_2$—$CH_2$—NRH—, —CO—NRH—$CH_2$—, —$CH_2$—NRHCO—, —O—$CH_2$—$CH_2$—S—, —S—$CH_2$—$CH_2$—O—, —S—$CH_2$—$CH_2$—S—, —$CH_2$—$SO_2$—$CH_2$—, —$CH_2$—CO—NRH—, —O—$CH_2$—$CH_2$—NRH—CO—, —$CH_2$—$NCH_3$—O—$CH_2$—, where RH is selected from hydrogen and $C_{1-4}$-alkyl.

Nuclease resistant linkages, such as phosphothioate linkages, are particularly useful in oligonucleotide regions capable of recruiting nuclease when forming a duplex with the target nucleic acid, such as region G for gapmers, or the non-modified nucleoside region of headmers and tailmers. Phosphorothioate linkages may, however, also be useful in non-nuclease recruiting regions and/or affinity enhancing regions such as regions F and F' for gapmers, or the modified nucleoside region of headmers and tailmers.

Each of the design regions may however comprise internucleoside linkages other than phosphorothioate, such as phosphodiester linkages, in particularly in regions where modified nucleosides, such as LNA, protect the linkage against nuclease degradation. Inclusion of phosphodiester linkages, such as one or two linkages, particularly between or adjacent to modified nucleoside units (typically in the non-nuclease recruiting regions) can modify the bioavailability and/or bio-distribution of an oligonucleotide—see WO2008/113832, incorporated herein by reference.

In an embodiment all the internucleoside linkages in the oligonucleotide are phosphorothioate and/or boranophosphate linkages. In some embodiment, all the internucleoside linkages in the oligonucleotide are phosphorothioate linkages.

Modulation of Expression

The term "modulation of expression" as used herein is to be understood as an overall term for an oligonucleotide's ability to alter the amount of a nucleic acid target when compared to the amount of the nucleic acid target before administration of the oligonucleotide. Alternatively modulation of expression may be determined by reference to a control experiment. It is generally understood that the control is an individual or target cell treated with a saline composition or an individual or target cell treated with a non-targeting oligonucleotide (mock). It may however also be an individual treated with the standard of care.

One type of modulation is an oligonucleotide's ability to inhibit, down-regulate, reduce, suppress, remove, stop, block, prevent, lessen, lower, avoid or terminate expression of the nucleic acid target e.g. by degradation of mRNA or blockage of transcription. Another type of modulation is an oligonucleotide's ability to restore, increase or enhance expression of nucleic acid target e.g. by repair of splice sites or prevention of splicing or removal or blockage of inhibitory mechanisms such as microRNA repression.

In some embodiments of the invention, when the target of the oligonucleotide of the invention is present in the primary mammalian hepatocyte cells, the method of the invention may further comprise the step of determining the level of target modulation (e.g. inhibit for siRNAs or antisense oligonucleotides) in the population of primary mammalian hepatocyte cells after treatment with the oligonucleotides (e.g. this may occur in parallel or as part of the measurement of the at least one biomarker step). In this regard the method of the invention may be used to determine the comparative potency or effectiveness of the oligonucleotide and the comparative toxicity, allowing for the selection of potent non-toxic compounds for use in vivo. It will be understood that the determination of compound potency/effectiveness may be performed in a separate in vitro experiment, either in the mammalian hepatocyte cells, or in other cell types, particularly cells which are expressing the target. In vitro gymnotic assays in cells which are expressing the target may therefore be used.

Modified Oligonucleotides

Non modified DNA and RNA molecules are rapidly degraded in vivo, and as such are of little use therapeutically. Typically, the oligonucleotide(s) used in the method of the invention are therefore modified. One widely used modification is the use of phosphorothioate internucleoside linkages, which is known to stabilise oligonucleotides from nucleolytic degradation, as well as providing desirable pharmacological properties. In some embodiments the oligonucleotide(s) comprise phosphorothioate internucleoside linkages. Another desirable modification are those which confer higher affinity of the oligonucleotide, so called high affinity modified nucleotides, which include bicyclic "LNA" nucleosides as well as numerous 2' substituted nucleosides.

High Affinity Modified Nucleosides

In some embodiments, the oligonucleotide comprises one or more high affinity modified nucleoside. A high affinity modified nucleoside is a modified nucleotide which, when incorporated into the oligonucleotide enhances the affinity of the oligonucleotide for its complementary target, for example as measured by the melting temperature ($T^m$). A high affinity modified nucleoside of the present invention preferably result in an increase in melting temperature between +0.5 to +12° C., more preferably between +1.5 to +10° C. and most preferably between +3 to +8° C. per modified nucleoside. Numerous high affinity modified nucleosides are known in the art and include for example, many 2' substituted nucleosides as well as locked nucleic acids (LNA) (see e.g. Freier & Altmann; Nucl. Acid Res., 1997, 25, 4429-4443 and Uhlmann; Curr. Opinion in Drug Development, 2000, 3(2), 293-213).

Sugar Modifications

The oligonucleotide(s) may comprise one or more nucleosides which have a modified sugar moiety, i.e. a modification of the sugar moiety when compared to the ribose sugar moiety found in DNA and RNA.

Numerous nucleosides with modification of the ribose sugar moiety have been made, primarily with the aim of improving certain properties of oligonucleotides, such as affinity and/or nuclease resistance.

Such modifications include those where the ribose ring structure is modified, e.g. by replacement with a hexose ring (HNA), or a bicyclic ring, which typically have a biradicle bridge between the C2 and C4 carbons on the ribose ring (LNA), or an unlinked ribose ring which typically lacks a bond between the C2 and C3 carbons (e.g. UNA). Other sugar modified nucleosides include, for example, bicyclohexose nucleic acids (WO2011/017521) or tricyclic nucleic acids (WO2013/154798). Modified nucleosides also include nucleosides where the sugar moiety is replaced with a non-sugar moiety, for example in the case of peptide nucleic acids (PNA), or morpholino nucleic acids.

Sugar modifications also include modifications made via altering the substituent groups on the ribose ring to groups other than hydrogen, or the 2'-OH group naturally found in DNA and RNA nucleosides. Substituents may, for example be introduced at the 2', 3', 4' or 5' positions. Nucleosides with modified sugar moieties also include 2' modified nucleosides, such as 2' substituted nucleosides. Indeed, much focus has been spent on developing 2' substituted nucleosides, and numerous 2' substituted nucleosides have been found to have beneficial properties when incorporated into oligonucleotides, such as enhanced nucleoside resistance and enhanced affinity.

2' Modified Nucleosides.

A 2' sugar modified nucleoside is a nucleoside which has a substituent other than H or —OH at the 2' position (2' substituted nucleoside) or comprises a 2' linked biradicle, and includes 2' substituted nucleosides and LNA (2'-4' biradicle bridged) nucleosides. For example, the 2' modified sugar may provide enhanced binding affinity and/or increased nuclease resistance to the oligonucleotide. Examples of 2' substituted modified nucleosides are 2'-O-alkyl-RNA, 2'-O-methyl-RNA, 2'-alkoxy-RNA, 2'-O-methoxyethyl-RNA (MOE), 2'-amino-DNA, 2'-Fluoro-RNA, and 2'-F-ANA nucleoside. For further examples, please see e.g. Freier & Altmann; Nucl. Acid Res., 1997, 25, 4429-4443 and Uhlmann; Curr. Opinion in Drug Development, 2000, 3(2), 293-213, and Deleavey and Damha, Chemistry and Biology 2012, 19, 937. Below are illustrations of some 2' substituted modified nucleosides.

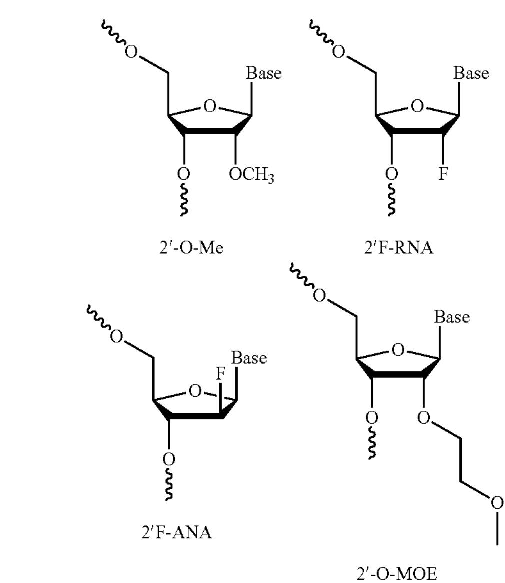

-continued

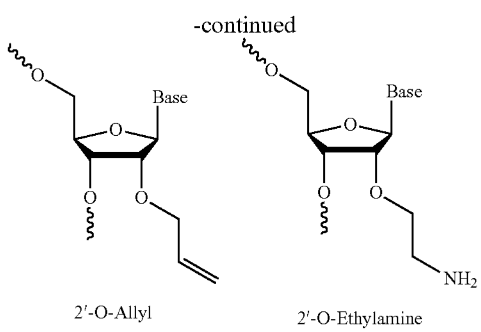

2′-O-Allyl 2′-O-Ethylamine

Locked Nucleic Acid Nucleosides (LNA).

In some embodiments oligonucleotides are LNA oligonucleotides, i.e. they comprise at least one LNA nucleoside.

LNA monomers (also referred to as bicyclic nucleic acids, BNA) are nucleosides where there is a biradical between the 2' and 4' position of the ribose ring. The 2'-4' biradical is also referred to as a bridge. LNA monomers, when incorporated into a oligonucleotides are known to enhance the binding affinity of the oligonucleotide to a complementary DNA or RNA sequence, typically measured or calculated as an increase in the temperature required to melt the oligonucleotide/target duplex ($T_m$).

The LNA oligomer may be a single stranded antisense oligonucleotide.

The LNA used in the oligonucleotide compounds of the invention may have the structure of the general formula I Formula 1

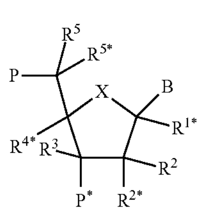

wherein for all chiral centers, asymmetric groups may be found in either R or S orientation;

wherein X is selected from —O—, —S—, —N($R^{N*}$)—, —C($R^6R^{6*}$)—, such as, in some embodiments —O—;

B is selected from hydrogen, optionally substituted $C_{1-4}$-alkoxy, optionally substituted $C_{1-4}$-alkyl, optionally substituted $C_{1-4}$-acyloxy, nucleobases including naturally occurring and nucleobase analogues, DNA intercalators, photochemically active groups, thermochemically active groups, chelating groups, reporter groups, and ligands; preferably, B is a nucleobase or nucleobase analogue;

P designates an internucleotide linkage to an adjacent monomer, or a 5'-terminal group, such internucleotide linkage or 5'-terminal group optionally including the substituent $R^5$ or equally applicable the substituent $R^{5*}$;

P* designates an internucleotide linkage to an adjacent monomer, or a 3'-terminal group;

$R^{4*}$ and $R^{2*}$ together designate a bivalent linker group consisting of 1-4 groups/atoms selected from —C($R^aR^b$)—, —C($R^a$)═C($R^b$)—, —C($R^a$)═N—, —O—, —Si($R^a$)$_2$—, —S—, —$SO_2$—, —N($R^a$)—, and >C═Z, wherein Z is selected from —O—, —S—, and —N($R^a$)—, and $R^a$ and $R^b$ each is independently selected from hydrogen, optionally substituted $C_{1-12}$-alkyl, optionally substituted $C_{2-12}$-alkenyl, optionally substituted $C_{2-12}$-alkynyl, hydroxy, optionally substituted $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted and where two geminal substituents $R^a$ and $R^b$ together may designate optionally substituted methylene (═$CH_2$), wherein for all chiral centers, asymmetric groups may be found in either R or S orientation, and;

each of the substituents $R^{1*}$, $R^2$, $R^3$, $R^5$, $R^{5*}$, $R^6$ and $R^{6*}$, which are present is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted, and where two geminal substituents together may designate oxo, thioxo, imino, or optionally substituted methylene; wherein $R^N$ is selected from hydrogen and $C_{1-4}$-alkyl, and where two adjacent (non-geminal) substituents may designate an additional bond resulting in a double bond; and $R^{N*}$, when present and not involved in a biradical, is selected from hydrogen and $C_{1-4}$-alkyl;

and basic salts and acid addition salts thereof. For all chiral centers, asymmetric groups may be found in either R or S orientation.

In some embodiments, $R^{4*}$ and $R^{2*}$ together designate a biradical consisting of a groups selected from the group consisting of C($R^aR^b$)—C($R^aR^b$)—, C($R^aR^b$)—O—, C($R^aR^b$)—N$R^a$—, C($R^aR^b$)—S—, and C($R^aR^b$)—C($R^aR^b$)—O—, wherein each $R^a$ and $R^b$ may optionally be independently selected. In some embodiments, $R^a$ and $R^b$ may be, optionally independently selected from the group consisting of hydrogen and $_{C1-6}$alkyl, such as methyl, such as hydrogen.

In some embodiments, $R^{4*}$ and $R^{2*}$ together designate the biradical —O—CH($CH_2OCH_3$)—(2'O-methoxyethyl bicyclic nucleic acid—Seth at al., 2010, J. Org. Chem)—in either the R— or S— configuration.

In some embodiments, $R^{4*}$ and $R^{2*}$ together designate the biradical —O—CH($CH_2CH_3$)—(2'O-ethyl bicyclic nucleic acid—Seth at al., 2010, J. Org. Chem).—in either the R— or S— configuration.

In some embodiments, $R^{4*}$ and $R^{2*}$ together designate the biradical —O—CH($CH_3$)—. -in either the R— or S— configuration. In some embodiments, $R^{4*}$ and $R^{2*}$ together designate the biradical —O—$CH_2$—O—$CH_2$—-(Seth at al., 2010, J. Org. Chem). In some embodiments, $R^{4*}$ and $R^{2*}$ together designate the biradical —O—NR—$CH_3$—-(Seth at al., 2010, J. Org. Chem).

In some embodiments, the LNA units have a structure selected from the following group:

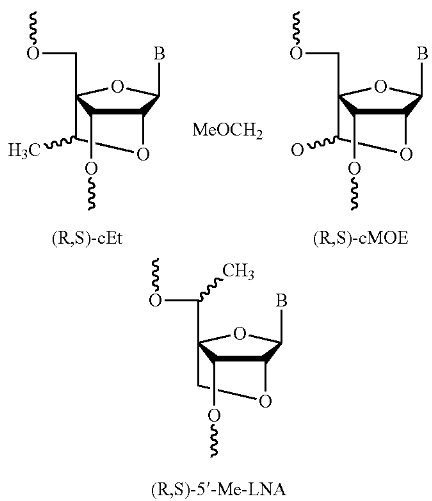

In some embodiments, $R^{1*}$, $R^2$, $R^3$, $R^5$, $R^{5*}$ are independently selected from the group consisting of hydrogen, halogen, $C_{1-6}$ alkyl, substituted $C_{1-6}$ alkyl, $C_2$-$_6$ alkenyl, substituted $C_{2-6}$ alkenyl, $C_{2-6}$ alkynyl or substituted $C_{2-6}$ alkynyl, $C_{1-6}$ alkoxyl, substituted $C_{1-6}$ alkoxyl, acyl, substituted acyl, $C_{1-6}$ aminoalkyl or substituted $C_{1-6}$ aminoalkyl. For all chiral centers, asymmetric groups may be found in either R or S orientation.

In some embodiments, $R^{1*}$, $R^2$, $R^3$, $R^5$, $R^{5*}$ are hydrogen.

In some embodiments, $R^{1*}$, $R^2$, $R^3$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$ alkoxyl, substituted $C_{1-6}$ alkoxyl, acyl, substituted acyl, $C_{1-6}$ aminoalkyl or substituted $C_{1-6}$ aminoalkyl. For all chiral centers, asymmetric groups may be found in either R or S orientation.

In some embodiments, $R^{1*}$, $R^2$, $R^3$ are hydrogen.

In some embodiments, $R^5$ and $R^{5*}$ are each independently selected from the group consisting of H, —$CH_3$, —$CH_2$—$CH_3$, —$CH_2$—O—$CH_3$, and —CH═$CH_2$. Suitably in some embodiments, either $R^5$ or $R^{5*}$ are hydrogen, where as the other group ($R^5$ or $IR^{5*}$ respectively) is selected from the group consisting of $C_1$-$_5$ alkyl, $C_{2-6}$ alkenyl, $C_{2-6}$ alkynyl, substituted $C_{1-6}$ alkyl, substituted $C_{2-6}$ alkenyl, substituted $C_{2-6}$ alkynyl or substituted acyl (—C(═O)—); wherein each substituted group is mono or poly substituted with substituent groups independently selected from halogen, $C_{1-6}$ alkyl, substituted $C_{1-6}$ alkyl, $C_{2-6}$ alkenyl, substituted $C_{2-6}$ alkenyl, $C_{2-6}$ alkynyl, substituted $C_{2-6}$ alkynyl, $OJ_1$, $SJ_1$, $NJ_1J_2$, $N_3$, $COOJ_1$, CN, O—C(═O)$NJ_1J_2$, N(H)C(═NH)NJ,$J_2$ or N(H)C(═X)N(H)$J_2$ wherein X is O or S; and each $J_1$ and $J_2$ is, independently, H, $C_{1-6}$ alkyl, substituted $C_{1-6}$ alkyl, $C_{2-6}$ alkenyl, substituted $C_{2-6}$ alkenyl, $C_{2-6}$ alkynyl, substituted $C_{2-6}$ alkynyl, $C_{1-6}$ aminoalkyl, substituted $C_{1-6}$ aminoalkyl or a protecting group. In some embodiments either $R^5$ or $R^{5*}$ is substituted $C_{1-6}$ alkyl. In some embodiments either $R^5$ or $R^{5*}$ is substituted methylene wherein preferred substituent groups include one or more groups independently selected from F, $NJ_1J_2$, $N_3$, CN, $OJ_1$, $SJ_1$, O—C(═O)$NJ_1J_2$, N(H)C(═NH)NJ, $J_2$ or N(H)C(O)N(H)$J_2$. In some embodiments each $J_1$ and $J_2$ is, independently H or $C_{1-6}$ alkyl. In some embodiments either $R^5$ or $R^{5*}$ is methyl, ethyl or methoxymethyl. In some embodiments either $R^5$ or $R^{5*}$ is methyl. In a further embodiment either $R^5$ or $R^{5*}$ is ethylenyl. In some embodiments either $R^5$ or $R^{5*}$ is substituted acyl. In some embodiments either $R^5$ or $R^{5*}$ is C(═O)$NJ_1J_2$. For all chiral centers, asymmetric groups may be found in either R or S orientation. Such 5' modified bicyclic nucleotides are disclosed in WO 2007/134181, which is hereby incorporated by reference in its entirety.

In some embodiments B is a nucleobase, including nucleobase analogues and naturally occurring nucleobases, such as a purine or pyrimidine, or a substituted purine or substituted pyrimidine, such as a nucleobase referred to herein, such as a nucleobase selected from the group consisting of adenine, cytosine, thymine, adenine, uracil, and/or a modified or substituted nucleobase, such as 5-thiazolo-uracil, 2-thio-uracil, 5-propynyl-uracil, 2'thio-thymine, 5-methyl cytosine, 5-thiozolo-cytosine, 5-propynyl-cytosine, and 2,6-diaminopurine.

In some embodiments, $R^{4*}$ and $R^{2*}$ together designate a biradical selected from —C($R^aR^b$)—O—, —C($R^aR^b$)—C($R^cR^d$)—O—, —C($R^aR^b$)—C($R^cR^d$)—C($R^eR^f$)—O—, —C($R^aR^b$)—O—C($R^cR^d$)—, —C($R^aR^b$)—O—C($R^cR^d$)—O—, —C($R^aR^b$)—C($R^cR^d$)—, —C($R^aR^b$)—C($R^cR^d$)—C($R^eR^f$)—, —C($R^a$)═C($R^b$)—C($R^cR^d$)—, —C($R^aR^b$)—N($R^c$)—, —C($R^aR^b$)—C($R^cR^d$)—N($R^e$)—, —C($R^aR^b$)—N($R^c$)—O—, and —C($R^aR^b$)—S—, —C($R^aR^b$)—C($R^cR^d$)—S—, wherein $R^a$, $R^b$, $R^c$, $R^d$, $R^e$, and $R^f$ each is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted and where two geminal substituents $R^a$ and $R^b$ together may designate optionally substituted methylene (═$CH_2$). For all chiral centers, asymmetric groups may be found in either R or S orientation.

In a further embodiment $R^{4*}$ and $R^{2*}$ together designate a biradical (bivalent group) selected from —$CH_2$—O—, —$CH_2$—S—, —$CH_2$—NH—, —$CH_2$—N($CH_3$)—, —$CH_2$—$CH_2$—O—, —$CH_2$—CH($CH_3$)—, —$CH_2$—$CH_2$—S—, —$CH_2$—$CH_2$—NH—, —$CH_2$—$CH_2$—$CH_2$—, —$CH_2$—$CH_2$—$CH_2$—O—, —$CH_2$—$CH_2$—CH($CH_3$)—, —CH═CH—$CH_2$—, —$CH_2$—O—$CH_2$—O—, —$CH_2$—NH—O—, —$CH_2$—N($CH_3$)—O—, —$CH_2$—O—$CH_2$—, —CH($CH_3$)—O—, and —CH($CH_2$—O—$CH_3$)—O—, and/or, —$CH_2$—$CH_2$—, and —CH═CH— For all chiral centers, asymmetric groups may be found in either R or S orientation.

In some embodiments, $R^{4*}$ and $R^{2*}$ together designate the biradical C($R^aR^b$)—N($R^c$)—O—, wherein $R^a$ and $R^b$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$ alkoxyl, substituted $C_{1-6}$ alkoxyl, acyl, substituted acyl, $C_{1-6}$ aminoalkyl or substituted $C_{1-6}$ aminoalkyl, such as hydrogen, and; wherein $R^c$ is selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$ alkoxyl, substituted $C_{1-6}$ alkoxyl, acyl, substituted acyl, $C_{1-6}$ aminoalkyl or substituted $C_{1-6}$ aminoalkyl, such as hydrogen.

In some embodiments, $R^{4*}$ and $R^{2*}$ together designate the biradical $C(R^aR^b)$—O—$C(R^cR^d)$ —O—, wherein $R^a$, $R^b$, $R^c$, and $R^d$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$ alkoxyl, substituted $C_{1-6}$ alkoxyl, acyl, substituted acyl, $C_{1-6}$ aminoalkyl or substituted $C_{1-6}$ aminoalkyl, such as hydrogen.

In some embodiments, $R^{4*}$ and $R^{2*}$ form the biradical —CH(Z)—O—, wherein Z is selected from the group consisting of $C_{1-6}$ alkyl, $C_{2-6}$ alkenyl, $C_{2-6}$ alkynyl, substituted $C_{1-6}$ alkyl, substituted $C_{2-6}$ alkenyl, substituted $C_{2-6}$ alkynyl, acyl, substituted acyl, substituted amide, thiol or substituted thio; and wherein each of the substituted groups, is, independently, mono or poly substituted with optionally protected substituent groups independently selected from halogen, oxo, hydroxyl, $OJ_1$, $NJ_1J_2$, $SJ_1$, $N_3$, $OC(=X)J_1$, $OC(=X)NJ_1J_2$, $NJ^3C(=X)NJ_1J_2$ and CN, wherein each $J_1$, $J_2$ and $J_3$ is, independently, H or $C_{1-6}$ alkyl, and X is O, S or $NJ_1$. In some embodiments Z is $C_{1-6}$ alkyl or substituted $C_{1-6}$ alkyl. In some embodiments Z is methyl. In some embodiments Z is substituted $C_{1-6}$ alkyl. In some embodiments said substituent group is $C_{1-6}$ alkoxy. In some embodiments Z is $CH_3OCH_2$—. For all chiral centers, asymmetric groups may be found in either R or S orientation. Such bicyclic nucleotides are disclosed in U.S. Pat. No. 7,399,845 which is hereby incorporated by reference in its entirety. In some embodiments, $R^{1*}$, $R^2$, $R^3$, $R^5$, $R^{5*}$ are hydrogen. In some some embodiments, $R^{1*}$, $R^2$, $R^{3*}$ are hydrogen, and one or both of $R^5$, $R^{5*}$ may be other than hydrogen as referred to above and in WO 2007/134181.

In some embodiments, $R^{4*}$ and $R^{2*}$ together designate a biradical which comprise a substituted amino group in the bridge such as consist or comprise of the biradical —$CH_2$—$N(R^c)$—, wherein $R^c$ is $C_{1-12}$alkyloxy. In some embodiments $R^{4*}$ and $R^{2*}$ together designate a biradical-$Cq_3q_4$-NOR—, wherein $q_3$ and $q_4$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$ alkoxyl, substituted $C_{1-6}$ alkoxyl, acyl, substituted acyl, $C_{1-6}$ aminoalkyl or substituted $C_{1-6}$ aminoalkyl; wherein each substituted group is, independently, mono or poly substituted with substituent groups independently selected from halogen, $OJ_1$, $SJ_1$, $NJ_1J_2$, $COOJ_1$, CN, O—$C(=O)NJ_1J_2$, N(H)C$(=NH)N\ J_1J_2$ or N(H)C(=X=N(H)$J_2$ wherein X is O or S; and each of $J_1$ and $J_2$ is, independently, H, $C_{1-6}$ alkyl, $C_{2-6}$ alkenyl, $C_{2-6}$ alkynyl, $C_{1-6}$ aminoalkyl or a protecting group. For all chiral centers, asymmetric groups may be found in either R or S orientation. Such bicyclic nucleotides are disclosed in WO2008/150729 which is hereby incorporated by reference in its entirety. In some embodiments, $R^{1*}$, $R^2$, $R^3$, $R^5$, $R^{5*}$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$ alkoxyl, substituted $C_{1-6}$ alkoxyl, acyl, substituted acyl, $C_{1-6}$ aminoalkyl or substituted $C_{1-6}$ aminoalkyl. In some embodiments, $R^{1*}$, $R^2$, $R^3$, $R^5$, $R^{5*}$ are hydrogen. In some embodiments, $R^{1*}$, $R^2$, $R^3$ are hydrogen and one or both of $R^5$, $R^{5*}$ may be other than hydrogen as referred to above and in WO 2007/134181. In some embodiments $R^{4*}$ and $R^{2*}$ together designate a biradical (bivalent group) $C(R^aR^b)$—O—, wherein $R^a$ and $R^b$ are each independently halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_1$ $SJ_1$, $SOJ_1$, $SO_2J_1$, $NJ_1J_2$, $N_3$, CN, $C(=O)OJ_1$, $C(=O)NJ_1J_2$, $C(=O)J_1$, O—C(=O)$NJ_1J_2$, N(H)C(=NH)$NJ_1J_2$, N(H)C(=O)$NJ_1J_2$ or N(H)C(=S)$NJ_1J_2$; or $R^a$ and $R^b$ together are =C(q3)(q4); $q_3$ and $q_4$ are each, independently, H, halogen, $C_1$-$C_{12}$alkyl or substituted $C_1$-$C_{12}$ alkyl; each substituted group is, independently, mono or poly substituted with substituent groups independently selected from halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $OJ_1$, $SJ_1$, $NJ_1J_2$, $N_3$, CN, $C(=O)OJ_1$, $C(=O)NJ_1J_2$, $C(=O)J_1$, O—C(=O)$NJ_1J_2$, N(H)C(=O)$NJ_1J_2$ or N(H)C(=S)$NJ_1J_2$ and; each $J_1$ and $J_2$ is, independently, H, C1-$C_6$ alkyl, substituted C1-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, C1-$C_6$ aminoalkyl, substituted C1-$C_6$ aminoalkyl or a protecting group. Such compounds are disclosed in WO2009006478A, hereby incorporated in its entirety by reference.

In some embodiments, $R^{4*}$ and $R^{2*}$ form the biradical-Q-, wherein Q is $C(q_1)(q_2)C(q_3)(q_4)$, $C(q_1)=C(q_3)$, $C[=C(q_1)(q_2)]$-$C(q_3)(q_4)$ or $C(q_1)(q_2)$ —$C[=C(q_3)(q_4)]$; $q_1$, $q_2$, $q_3$, $q_4$ are each independently. H, halogen, $C_{1-12}$ alkyl, substituted $C_{1-12}$ alkyl, $C_{2-12}$ alkenyl, substituted $C_{1-12}$ alkoxy, $OJ_1$, $SJ_1$, $SOJ_1$, $SO_2J_1$, $NJ_1J_2$, $N_3$, CN, $C(=O)OJ_1$, C(=O)—$NJ_1J_2$, C(=O) $J_1$, —C(=O)$NJ_1J_2$, N(H)C(=NH)$NJ_1J_2$, N(H)C(=O)$NJ_1J_2$ or N(H)C(=S)$NJ_1J_2$; each $J_1$ and $J_2$ is, independently, H, $C_{1-6}$ alkyl, $C_{2-6}$ alkenyl, $C_{2-6}$ alkynyl, $C_{1-6}$ aminoalkyl or a protecting group; and, optionally wherein when Q is $C(q_1)(q_2)(q_3)(q_4)$ and one of $q_3$ or $q_4$ is $CH_3$ then at least one of the other of $q_3$ or $q_4$ or one of $q_1$ and $q_2$ is other than H. In some embodiments, $R^{1*}$, $R^2$, $R^3$, $R^5$, $R^{5*}$ are hydrogen. For all chiral centers, asymmetric groups may be found in either R or S orientation. Such bicyclic nucleotides are disclosed in WO2008/154401 which is hereby incorporated by reference in its entirety. In some embodiments, $R^{1*}$, $R^2$, $R^3$, $R^5$, $R^{5*}$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$alkoxyl, substituted $C_{1-6}$alkoxyl, acyl, substituted acyl, $C_{1-6}$ aminoalkyl or substituted $C_{1-6}$ aminoalkyl. In some embodiments, $R^{1*}$, $R^2$, $R^3$, $R^5$, $R^{5*}$ are hydrogen. In some embodiments, $R^{1*}$, $R^2$, $R^3$ are hydrogen and one or both of $R^5$, $R^{5*}$ may be other than hydrogen as referred to above and in WO 2007/134181 or WO2009/067647 (alpha-L-bicyclic nucleic acids analogs).

Further bicyclic nucleoside analogues and their use in antisense oligonucleotides are disclosed in WO2011 115818, WO2011/085102, WO2011/017521, WO09100320, WO10036698, WO09124295 & WO09006478. Such nucleoside analogues may in some aspects be useful in the compounds of present invention.

In some embodiments the LNA used in the oligonucleotide compounds of the invention preferably has the structure of the general formula II:

Formula II

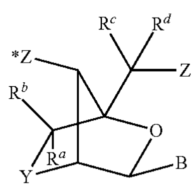

wherein Y is selected from the group consisting of —O—, —$CH_2$O—, —S—, —NH—, N($R^e$) and/or —$CH_2$—; Z and Z* are independently selected among an internucleotide linkage, $R^H$, a terminal group or a protecting group; B constitutes a natural or non-natural nucleotide base moiety (nucleobase), and $R^H$ is selected from hydrogen and $C_{1-4}$-alkyl; $R^a$, $R^b$ $R^c$, $R^d$ and $R^e$ are, optionally independently, selected from the group consisting of hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkoxyalkyl, $C_{2-12}$-alkenyloxy, carboxy, $C_{1-12}$-alkoxycarbonyl, $C_{1-12}$ alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$ alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted and where two geminal substituents $R^a$ and $R^b$ together may designate optionally substituted methylene (=$CH_2$); and $R^H$ is selected from hydrogen and $C_{1-4}$-alkyl. In some embodiments $R^a$, $R^b$ $R^c$, $R^d$ and $R^e$ are, optionally independently, selected from the group consisting of hydrogen and $C_{1-6}$ alkyl, such as methyl. For all chiral centers, asymmetric groups may be found in either R or S orientation, for example, two exemplary stereochemical isomers include the beta-D and alpha-L isoforms, which may be illustrated as follows:

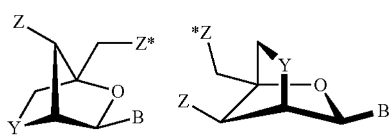

Specific exemplary LNA units are shown below:

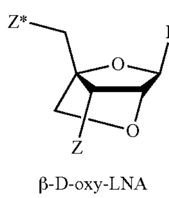

β-D-oxy-LNA

α-L-Oxy-LNA

-continued

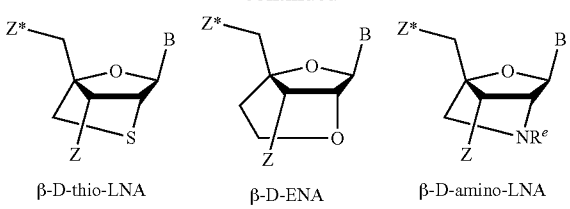

β-D-thio-LNA β-D-ENA β-D-amino-LNA

The term "thio-LNA" comprises a locked nucleotide in which Y in the general formula above is selected from S or —$CH_2$—S—. Thio-LNA can be in both beta-D and alpha-L-configuration.

The term "amino-LNA" comprises a locked nucleotide in which Y in the general formula above is selected from —N(H)—, N(R)—, $CH_2$—N(H)—, and —$CH_2$—N(R)— where R is selected from hydrogen and $C_{1-4}$-alkyl. Amino-LNA can be in both beta-D and alpha-L-configuration.

The term "oxy-LNA" comprises a locked nucleotide in which Y in the general formula above represents —O—. Oxy-LNA can be in both beta-D and alpha-L-configuration.

The term "ENA" comprises a locked nucleotide in which Y in the general formula above is —$CH_2$—O—(where the oxygen atom of —$CH_2$—O— is attached to the 2'-position relative to the base B). $R^e$ is hydrogen or methyl.

In some exemplary embodiments LNA is selected from beta-D-oxy-LNA, alpha-L-oxy-LNA, beta-D-amino-LNA and beta-D-thio-LNA, in particular beta-D-oxy-LNA.

Certain examples of LNA nucleosides are presented in Scheme 1.

Scheme 1

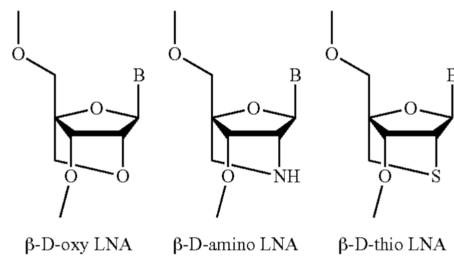

β-D-oxy LNA β-D-amino LNA β-D-thio LNA

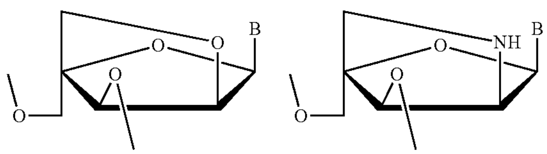

α-L-oxy LNA α-L-amino LNA

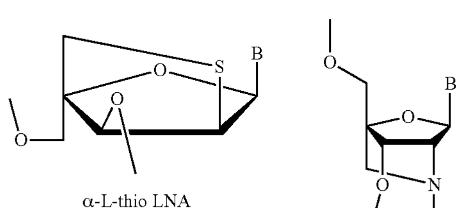

α-L-thio LNA

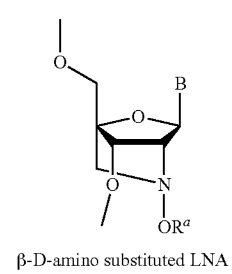

β-D-amino substituted LNA

-continued

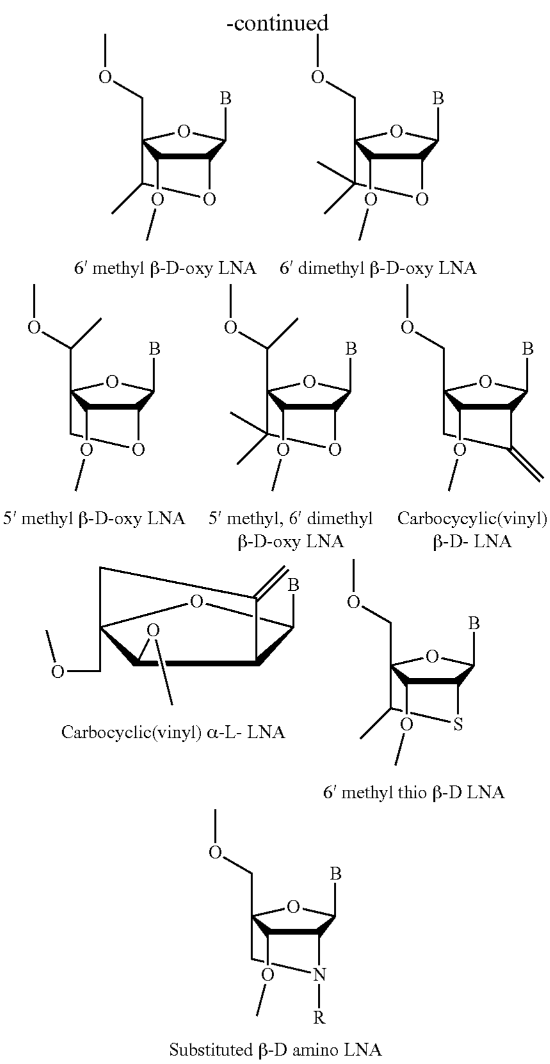

As illustrated in the examples, in some embodiments of the invention the LNA nucleosides in the oligonucleotides are beta-D-oxy-LNA nucleosides.

Gapmer

The term "gapmer" as used herein refers to an antisense oligonucleotide which comprises a region of RNase H recruiting oligonucleotides (gap) which is flanked 5' and 3' by regions which comprise one or more affinity enhancing modified nucleosides (flanks or wings). Various gapmer designs are described herein. Headmers and tailmers are oligonucleotides capable of recruiting RNase H where one of the flanks is missing, i.e. only one of the ends of the oligonucleotide comprises affinity enhancing modified nucleosides. For headmers the 3' flank is missing (i.e. the 5' flank comprises affinity enhancing modified nucleosides) and for tailmers the 5' flank is missing (i.e. the 3' flank comprises affinity enhancing modified nucleosides).

Gapmer Designs Gapmer oligonucleotides are widely used to inhibit a target RNA in a cell, such as a mRNA or viral RNA, via an antisense mechanism (and may therefore also be called antisense gapmer oligonucleotides). Gapmer oligonucleotides comprise a region of of at least 5 contiguous nucleotides which are capable or recruiting RNaseH (gap region), such as a region of DNA nucleotides, e.g. 6-14 DNA nucleotides, flanked 5' and 3' by regions which comprise affinity enhancing modified nucleosides, such as LNA or 2' substituted nucleotides. In some embodiments, the flanking regions may be 1-8 nucleotides in length.

In some embodiments, the parent and child oligonucleotides are gapmer oligonucleotides which comprise a central region (Y') of at least 5 or more contiguous nucleosides, such as at least 5 contiguous DNA nucleosides, and a 5' wing region (X') comprising of 1-6 high affinity nucleoside analogues, such as LNA nucleosides and a 3' wing region (Z') comprising of 1-6 high affinity nucleoside analogues, such as LNA 1-6 nucleosides. An LNA gapmer oligonucleotide is an oligonucleotide which comprises at least one LNA nucleoside in the wing regions, and may for example comprise at least one LNA in both the 5' and 3' wing regions.

In some embodiments, the oligonucleotide comprises or is a LNA gapmer e.g. comprises a contiguous stretch of nucleotides which is capable of recruiting an RNAse, such as RNAseH, such as a region of at least 5, 6 or 7 DNA nucleotides, referred to herein in as region Y' (Y'), wherein region Y' is flanked both 5' and 3' by regions of affinity enhancing nucleotide analogues, such as from 1-6 affinity enhancing nucleotide analogues 5' and 3' to the contiguous stretch of nucleotides which is capable of recruiting RNAse—these regions are referred to as regions X' (X') and Z' (Z') respectively. Examples of gapmers are disclosed in WO2004/046160, WO2008/113832, and WO2007/146511. The LNA gapmer oligomers of the invention comprise at least one LNA nucleoside in region X' or Z', such as at least one LNA nucleoside in region X' and at least one LNA nucleotide in region Z'.

In some embodiments, the monomers which are capable of recruiting RNAse are selected from the group consisting of DNA monomers, alpha-L-LNA monomers, C4' alkylayted DNA monomers (see PCT/EP2009/050349 and Vester et al., Bioorg. Med. Chem. Lett. 18 (2008) 2296-2300, hereby incorporated by reference), and UNA (unlinked nucleic acid) nucleotides (see Fluiter et al., Mol. Biosyst., 2009, 10, 1039 hereby incorporated by reference). UNA is unlocked nucleic acid, typically where the C2-C3 C—C bond of the ribose has been removed, forming an unlocked "sugar" residue. Preferably the gapmer comprises a (poly)nucleotide sequence of formula (5' to 3'), X'-Y'—Z', wherein; region X' (X') (5' region) consists or comprises of at least one high affinity nucleotide analogue, such as at least one LNA unit, such as from 1-6 affinity enhancing nucleotide analogues, such as LNA units, and; region Y' (Y') consists or comprises of at least five consecutive nucleotides which are capable of recruiting RNAse (when formed in a duplex with a complementary RNA molecule, such as the mRNA target), such as DNA nucleotides, and; region Z' (Z') (3'region) consists or comprises of at least one high affinity nucleotide analogue, such as at least one LNA unit, such as from 1-6 affinity enhancing nucleotide analogues, such as LNA units.

In some embodiments, region X' comprises or consists of 1, 2, 3, 4, 5 or 6 LNA units, such as 2-5 LNA units, such as 3 or 4 LNA units, and/or region Z' consists or comprises of 1, 2, 3, 4, 5 or 6 LNA units, such as from 2-5 LNA units, such as 3 or 4 LNA units.

In some embodiments, region X' may comprises of 1, 2, 3, 4, 5 or 6 2' substituted nucleotide analogues, such as 2'MOE; and/or region Z' comprises of 1, 2, 3, 4, 5 or 6 2'substituted nucleotide analogues, such as 2'MOE units.

In some embodiments, the substituent at the 2' position is selected from the group consisting of F; $CF_3$, CN, $N_3$, NO, $NO_2$, O—, S—, or N-alkyl; O—, S—, or N-alkenyl; O—, S— or Nalkynyl; or O—alkyl-O-alkyl, O-alkyl-N-alkyl or N-alkyl-O-alkyl wherein the alkyl, alkenyl and alkynyl may be substituted or unsubstituted $C_1$-$C_{10}$ alkyl or $C_2$-$C_{10}$ alkenyl and alkynyl. Examples of 2' substituents include, and are not limited to, $O(CH_2)$ $OCH_3$, and $O(CH_2)$ $NH_2$, wherein n is from 1 to about 10, e.g. MOE, DMAOE, DMAEOE.

In some embodiments Y' consists or comprises of 5, 6, 7, 8, 9, 10, 11 or 12 consecutive nucleotides which are capable of recruiting RNAse, or from 6-10, or from 7-9, such as 8 consecutive nucleotides which are capable of recruiting RNAse. In some embodiments region Y' consists or comprises at least one DNA nucleotide unit, such as 1-12 DNA units, preferably from 4-12 DNA units, more preferably from 6-10 DNA units, such as from 7-10 DNA units, such as 8, 9 or 10 DNA units.

In some embodiments region X' consist of 3 or 4 nucleotide analogues, such as LNA, region X' consists of 7, 8, 9 or 10 DNA units, and region Z' consists of 3 or 4 nucleotide analogues, such as LNA. Such designs include (X'-Y'—Z') 3-10-3, 3-10-4, 4-10-3, 3-9-3, 3-9-4, 4-9-3, 3-8-3, 3-8-4, 4-8-3, 3-7-3, 3-7-4, 4-7-3.

Further gapmer designs are disclosed in WO2004/046160, which is hereby incorporated by reference. WO2008/113832, which claims priority from U.S. provisional application 60/977,409 hereby incorporated by reference, refers to 'shortmer' gapmer oligomers. In some embodiments, oligomers presented here may be such shortmer gapmers.

In some embodiments the oligomer, e.g. region X', is consisting of a contiguous nucleotide sequence of a total of 10, 11, 12, 13 or 14 nucleotide units, wherein the contiguous nucleotide sequence comprises or is of formula (5'-3'), X'-Y'—Z' wherein; X' consists of 1, 2 or 3 affinity enhancing nucleotide analogue units, such as LNA units; Y' consists of 7, 8 or 9 contiguous nucleotide units which are capable of recruiting RNAse when formed in a duplex with a complementary RNA molecule (such as a mRNA target); and Z' consists of 1, 2 or 3 affinity enhancing nucleotide analogue units, such as LNA units.

In some embodiments the oligomer, comprises of a contiguous nucleotide sequence of a total of 10, 11, 12, 13, 14, 15 or 16 nucleotide units, wherein the contiguous nucleotide sequence comprises or is of formula (5'-3'), X'-Y'—Z' wherein; X' comprises of 1, 2, 3 or 4 LNA units; Y' consists of 7, 8, 9 or 10 contiguous nucleotide units which are capable of recruiting RNAse when formed in a duplex with a complementary RNA molecule (such as a mRNA target) e.g. DNA nucleotides; and Z' comprises of 1, 2, 3 or 4 LNA units.

In some embodiments X' consists of 1 LNA unit. In some embodiments X' consists of 2 LNA units. In some embodiments X' consists of 3 LNA units. In some embodiments Z' consists of 1 LNA units. In some embodiments Z' consists of 2 LNA units. In some embodiments Z' consists of 3 LNA units. In some embodiments Y' consists of 7 nucleotide units. In some embodiments Y' consists of 8 nucleotide units. In some embodiments Y' consists of 9 nucleotide units. In certain embodiments, region Y' consists of 10 nucleoside monomers. In certain embodiments, region Y' consists or comprises 1-10 DNA monomers. In some embodiments Y' comprises of from 1-9 DNA units, such as 2, 3, 4, 5, 6, 7, 8 or 9 DNA units. In some embodiments Y' consists of DNA units. In some embodiments Y' comprises of at least one LNA unit which is in the alpha-L configuration, such as 2, 3, 4, 5, 6, 7, 8 or 9 LNA units in the alpha-L-configuration. In some embodiments Y' comprises of at least one alpha-L-oxy LNA unit or wherein all the LNA units in the alpha-L-configuration are alpha-L-oxy LNA units. In some embodiments the number of nucleotides present in X'-Y'—Z' are selected from the group consisting of (nucleotide analogue units—region Y'—nucleotide analogue units): 1-8-1, 1-8-2, 2-8-1, 2-8-2, 3-8-3, 2-8-3, 3-8-2, 4-8-1, 4-8-2, 1-8-4, 2-8-4, or; 1-9-1, 1-9-2, 2-9-1, 2-9-2, 2-9-3, 3-9-2, 1-9-3, 3-9-1, 4-9-1, 1-9-4, or; 1-10-1, 1-10-2, 2-10-1, 2-10-2, 1-10-3, 3-10-1. In some embodiments the number of nucleotides in X'-Y'—Z' are selected from the group consisting of: 2-7-1, 1-7-2, 2-7-2, 3-7-3, 2-7-3, 3-7-2, 3-7-4, and 4-7-3. In certain embodiments, each of regions X' and Y' consists of three LNA monomers, and region Y' consists of 8 or 9 or 10 nucleoside monomers, preferably DNA monomers. In some embodiments both X' and Z' consists of two LNA units each, and Y' consists of 8 or 9 nucleotide units, preferably DNA units. In various embodiments, other gapmer designs include those where regions X' and/or Z' consists of 3, 4, 5 or 6 nucleoside analogues, such as monomers containing a 2'-O-methoxyethyl-ribose sugar (2'-MOE) or monomers containing a 2'-fluoro-deoxyribose sugar, and region Y' consists of 8, 9, 10, 11 or 12 nucleosides, such as DNA monomers, where regions X'-Y'—Z' have 3-9-3, 3-10-3, 5-10-5 or 4-12-4 monomers. Further gapmer designs are disclosed in WO 2007/146511A2, hereby incorporated by reference.

In the gapmer designs reported herein the gap region (Y') may comprise one or more stereodefined phosphorothaiote linkage, and the remaining internucleoside linkages of the gap region may e.g. be non-stereodefined internucleoside linkages, or may also be stereodefined phosphorothioate linkages.

Stereodefined Gapmers

In some embodiments, the child oligonucleotides are gapmers wherein at least one of the internucleoside linkages of central region are stereodefined, and optionally wherein the central region comprises both Rp and Sp internucleoside linkages.

A gapmer oligonucleotide may comprise a central region (Y') of at least 5 or more contiguous nucleosides capable of recruiting RNaseH, and a 5' wing region (X') comprising of 1-6 LNA nucleosides and a 3' wing region (Z') comprising of LNA 1-6 nucleosides. Suitably region Y' may have 6, 7, 8, 9, 10, 11, 12, 13 or 14 (e.g. 6-12) contiguous nucleotides, such as DNA nucleotides, and the nucleotides of regions X' and Z' adjacent to region Y' are LNA nucleotides. In some embodiments regions X' and Z' have 1-6 nucleotides at least one of which in each flank (X' and Z') are an LNA. In some embodiments all the nucleotides in region X' and region Z' are LNA nucleotides. In some embodiments the oligonucleotide of the invention comprises LNA and DNA nucleosides. In some embodiments, the oligonucleotide of the invention may be a mixed wing LNA gapmer where at least one of the LNA nucleosides in one of the wing regions (or at least one LNA in each wing) is replaced with a 2' substituted nucleoside, such as a 2'MOE nucleoside. In some embodiments the LNA gapmer does not comprise 2' substituted nucleosides in the wing regions. The internucleoside linkages between the nucleotides in the contiguous sequence of nucleotides of regions X'-Y'—Z' may be all phosphorothioate internucleoside linkages.

In some embodiments, in the child oligonucleotide(s) (and optionally the parent), at least one of the internucleoside linkages of central region are stereodefined, and wherein the central region comprises both Rp and Sp internucleoside linkages.

In some embodiments, in the child oligonucleotide(s) (and optionally the parent), the internucleoside linkages within region Y' are all stereodefined phosphorothioate internucleoside linkages. In some embodiments, in the child oligonucleotide(s) (and optionally the parent), the internucleoside linkages within region X' and Y' are stereodefined phosphorothioate internucleoside linkages. In some embodiments in the child oligonucleotide(s) (and optionally the parent), the internucleoside linkages between region X' and Y' and between region Y' and Z' are stereodefined phosphorothioate internucleoside linkages. In some embodiments in the child oligonucleotide(s) (and optionally the parent), all the internucleoside linkages within the contiguous nucleosides of regions X'-Y'—Z' are stereodefined phosphorothioate internucleoside linkages.

The introduction of at least one stereodefined phosphorothioate linkages in the gap region of an oligonucleotide may be used to modulate the biological profile of the oligonucleotide, for example it may modulate the toxicity profile. In some embodiments, 2, 3, 4 or 5 of the phosphorothioate linkages in the gap region in the child oligonucleotide(s) (and optionally the parent), are stereodefined. In some embodiments the remaining internucleoside linkages in the gap region are not stereodefined: They exist as a racemic mixture of Rp and Sp in the population of oligonucleotide species. In some embodiments in the child oligonucleotide(s) (and optionally the parent), the remaining internucleoside linkage in the oligonucleotide are not stereodefined. In some embodiments in the child oligonucleotide(s) (and optionally the parent), all the internucleoside linkages in the gap region are stereodefined. The gap region (referred to as Y') herein, is a region of nucleotides which is capable of recruiting RNaseH, and may for example be a region of at least 5 contiguous DNA nucleosides.

In some embodiments 1, 2, 3, 4, 5, 6, 7, 8, 9, 10, 11, 12, 13, or 14 of the linkages in the gap region of the oligomer are stereoselective phosphorothioate linkages.

In some embodiments 5%, 10%, 15%, 20%, 25%, 30%, 35%, 40%, 45%, 50%, 55%, 60%, 65%, 70%, 75%, 80%, 85%, 90%, or 95% of the linkages in the oligomer (e.g. gapmer) are stereoselective phosphorothioate linkages. In some embodiments all of the phosphorothioate linkages in the oligomer are stereoselective phosphorothioate linkages. In some embodiments the all the internucleoside linkages of the oligomer are stereodefined phosphorothioate linkages.

LNA Gapmer

The term LNA gapmer is a gapmer oligonucleotide wherein at least one of the affinity enhancing modified nucleosides is an LNA nucleoside. In some embodiments both flanks of the gapmer oligonucleotide comprise at least one LNA unit, and in some embodiments, all of the nucleoside of the flanks are LNA nucleosides.

In some embodiments, the 3' flank comprises at least one LNA nucleoside, preferably at least 2 LNA nucleosides. In some embodiments, the 5' flank comprises at least one LNA nucleoside. In some embodiments both the 5' and 3' flanking regions comprise a LNA nucleoside. In some embodiments all the nucleosides in the flanking regions are LNA nucleosides. Typically the LNA load of the flanks of LNA gapmers is lower than that for 2'substituted nucleosides, and examples of LNA gapmer designs include $[LNA]_{1-4}$-$[DNA]_{5-15}$-$[LNA]_{1-4}$.

In some embodiments, the gapmer is a so-called shortmer as described in WO2008/113832 incorporated herein by reference.

Further gapmer designs are disclosed in WO2004/046160, WO2007/146511 and incorporated by reference.

Mixed Wing Gapmer

The term mixed wing gapmer or mixed flank gapmer refers to a LNA gapmer wherein at least one of the flank regions comprise at least one LNA nucleoside and at least one non-LNA modified nucleoside, such as at least one DNA nucleoside or at least one 2' substituted modified nucleoside, such as, for example, 2'-O-alkyl-RNA, 2'-O-methyl-RNA, 2'-alkoxy-RNA, 2'-O-methoxyethyl-RNA (MOE), 2'-amino-DNA, 2'-Fluoro-RNA and 2'-F-ANA nucleoside(s). In some embodiments the mixed wing gapmer has one flank which comprises only LNA nucleosides (e.g. 5' or 3') and the other flank (3' or 5' respectfully) comprises 2' substituted modified nucleoside(s) and optionally LNA nucleosides.

Gapbreaker

The term "gapbreaker oligonucleotide" is used in relation to a gapmer capable of maintaining RNAseH recruitment even though the gap region is disrupted by a non-RNaseH recruiting nucleoside (a gap-breaker nucleoside, E) such that the gap region comprise less than 5 consecutive DNA nucleosides. Non-RNaseH recruiting nucleosides are for example nucleosides in the 3' endo conformation, such as LNA's where the bridge between C2' and C4' of the ribose sugar ring of a nucleoside is in the beta conformation, such as beta-D-oxy LNA or ScET nucleoside. The ability of gapbreaker oligonucleotide to recruit RNaseH is typically sequence or even compound specific—see Rukov et al. 2015 Nucl. Acids Res. Vol. 43 pp. 8476-8487, which discloses "gapbreaker" oligonucleotides which recruit RNaseH which in some instances provide a more specific cleavage of the target RNA.

In some embodiments, the oligonucleotide of the invention is a gapbreaker oligonucleotide. In some embodiments the gapbreaker oligonucleotide comprise a 5'-flank (F), a gap (G) and a 3'-flank (F'), wherein the gap is disrupted by a non-RNaseH recruiting nucleoside (a gap-breaker nucleoside, E) such that the gap contain at least 3 or 4 consecutive DNA nucleosides. The gap-breaker design is based upon the gapmer designs, e.g. those disclosed here (e.g. Region F corresponds to the X' region of the gapmer above, and region F' corresponds to the region Z' of the gapmer described herein), with the exception that the gap region (region Y') comprises a gap-breaker nucleoside. In some embodiments the gapbreaker nucleoside (E) is an LNA nucleoside where the bridge between C2' and C4' of the ribose sugar ring of a nucleoside is in the beta conformation and is placed within the gap region such that the gap-breaker LNA nucleoside is flanked 5' and 3' by at least 3 (5') and 3 (3') or at least 3 (5') and 4 (3') or at least 4(5') and 3(3') DNA nucleosides, and wherein the oligonucleotide is capable of recruiting RNaseH.

The gapbreaker oligonucleotide can be represented by the following formulae:

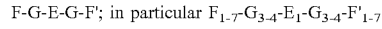
F-G-E-G-F'; in particular $F_{1-7}$-$G_{3-4}$-$E_1$-$G_{3-4}$-$F'_{1-7}$

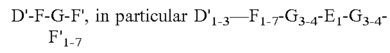
D'-F-G-F', in particular $D'_{1-3}$—$F_{1-7}$-$G_{3-4}$-$E_1$-$G_{3-4}$-$F'_{1-7}$

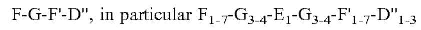
F-G-F'-D", in particular $F_{1-7}$-$G_{3-4}$-$E_1$-$G_{3-4}$-$F'_{1-7}$-$D''_{1-3}$

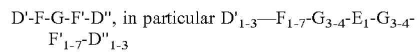
D'-F-G-F'-D", in particular $D'_{1-3}$—$F_{1-7}$-$G_{3-4}$-$E_1$-$G_{3-4}$-$F'_{1-7}$-$D''_{1-3}$ Where G represents DNA nucleosides and region D' and D" are optional and may additional 5' and/or 3' nucleosides, such as DNA nucleosides.

In some embodiments the gapbreaker nucleoside (E) is a LNA, beta-D-oxy LNA or ScET or another LNA nucleoside, such as beta-D-nucleoside disclosed herein.

RNase H Activity and Recruitment

The RNase H activity of an antisense oligonucleotide refers to its ability to recruit RNase H when in a duplex with a complementary RNA molecule. WO01/23613 provides in vitro methods for determining RNaseH activity, which may be used to determine the ability to recruit RNaseH. Typically an oligonucleotide is deemed capable of recruiting RNase H if it, when provided with a complementary target nucleic acid sequence, has an initial rate, as measured in pmol/l/min, of at least 5%, such as at least 10% or more than 20% of the of the initial rate determined when using a oligonucleotide having the same base sequence as the modified oligonucleotide being tested, but containing only DNA monomers with phosphorothioate linkages between all monomers in the oligonucleotide, and using the methodology provided by Example 91-95 of WO01/23613 (hereby incorporated by reference).

Efficacy

The oligonucleotide(s) identified by the method of the invention may be tested as part of the method of the invention to determine that they are effective antisense oligonucleotides, such as they are capable of inhibiting their target nucleic acid.

The method of the invention may therefore comprise an additional step of screening the library of (e.g. child) oligonucleotides for their efficacy in modulating, e.g. inhibiting, their target. Alternatively, the method of the invention may comprise an additional step of testing the selected oligonucleotides (e.g. stereodefined variants) with a reduced toxicity to determine their efficacy as an antisense oligonucleotide. In some embodiments, efficacy is determined by the oligonucleotides ability to recruit RNaseH, or in some embodiments may be the ability to modulate the expression of the target in a cell, in vitro, or in some embodiments, in vivo.

It is recognized that it is not necessary that the selected (e.g. child) oligonucleotides with reduced toxicity maintain the in vitro or in vivo potency of the parent oligonucleotide, but it is preferred that they are effective antisense oligonucleotides which have a reduced toxicity. Suitably, when evaluated in vivo, the therapeutic index of the oligonucleotide may be enhanced. Therapeutic index is typically calculated as the maximum tolerated dose (MTD) (e.g. for hepatotoxicity three times upper limit of normal) divided by the $ED_{50}$. For experimental purposes, assuming the target sequence is present in mice, MTD and $ED_{50}$ may be determined in mice in a seven day mouse study. If sequence conservation in mice is unfavourable, other model species may be used, e.g. rat, monkey, dog, pig or monkey (e.g. cynomolgus monkey).

In some embodiments, the selected (e.g. child) oligonucleotide(s) retain at least 25% such as at least 50%, such as at least 75%, such as at least 90% of the in vitro (e.g. $IC_{50}$) or in vivo (e.g. $ED_{50}$ or $EC_{50}$) potency of that of the parent. In some embodiments, the selected (e.g. child) oligonucleotide(s) identified in step c. have a similar in vitro (e.g. $IC_{50}$) or in vivo (e.g. $ED_{50}$ or $EC_{50}$) potency of that of the parent (i.e. +/− 10%), or have an enhanced in vitro (e.g. $IC_{50}$) or in vivo (e.g. $ED_{50}$ or $EC_{50}$) potency of that of the parent. The $IC_{50}$ or $ED_{50}$ should be evaluated in target cells which are expressing the intended target.

In some embodiments, the (e.g. child) oligonucleotide have an improved $EC_{50}$ value of the parent compound. In some embodiments, the child oligonucleotide retain a similar $EC_{50}$ value of the parent compound (i.e. +/− 10%). In some embodiments, the child oligonucleotide have an improved $EC_{50}$ value of the parent compound.

In some embodiments, the child oligonucleotide identified in step c. have no greater that a two fold higher (2×), or in some embodiments a three fold higher (3×) $EC_{50}$ value of the parent compound (i.e. +/− 10%). In some embodiments, the child oligonucleotide identified in step c. retain an $EC_{50}$ value of not larger than 3 to 10 times that of the parent compound.

Conjugate Moieties

In some embodiments, the conjugate moiety comprises or is a carbohydrate, non nucleosidic sugars, carbohydrate complexes. In some embodiments, the carbohydrate is selected from the group consisting of galactose, lactose, n-acetylgalactosamine, mannose, and mannose-6-phosphate.

In some embodiments, the conjugate moiety comprises or is selected from the group of protein, glycoproteins, polypeptides, peptides, antibodies, enzymes, and antibody fragments, In some embodiments, the conjugate moiety is a lipophilic moiety such as a moiety selected from the group consisting of lipids, phospholipids, fatty acids, and sterols.

In some embodiments, the conjugate moiety is selected from the group consisting of small molecules drugs, toxins, reporter molecules, and receptor ligands.

In some embodiments, the conjugate moiety is a polymer, such as polyethyleneglycol (PEG), polypropylene glycol.

Figure 2:
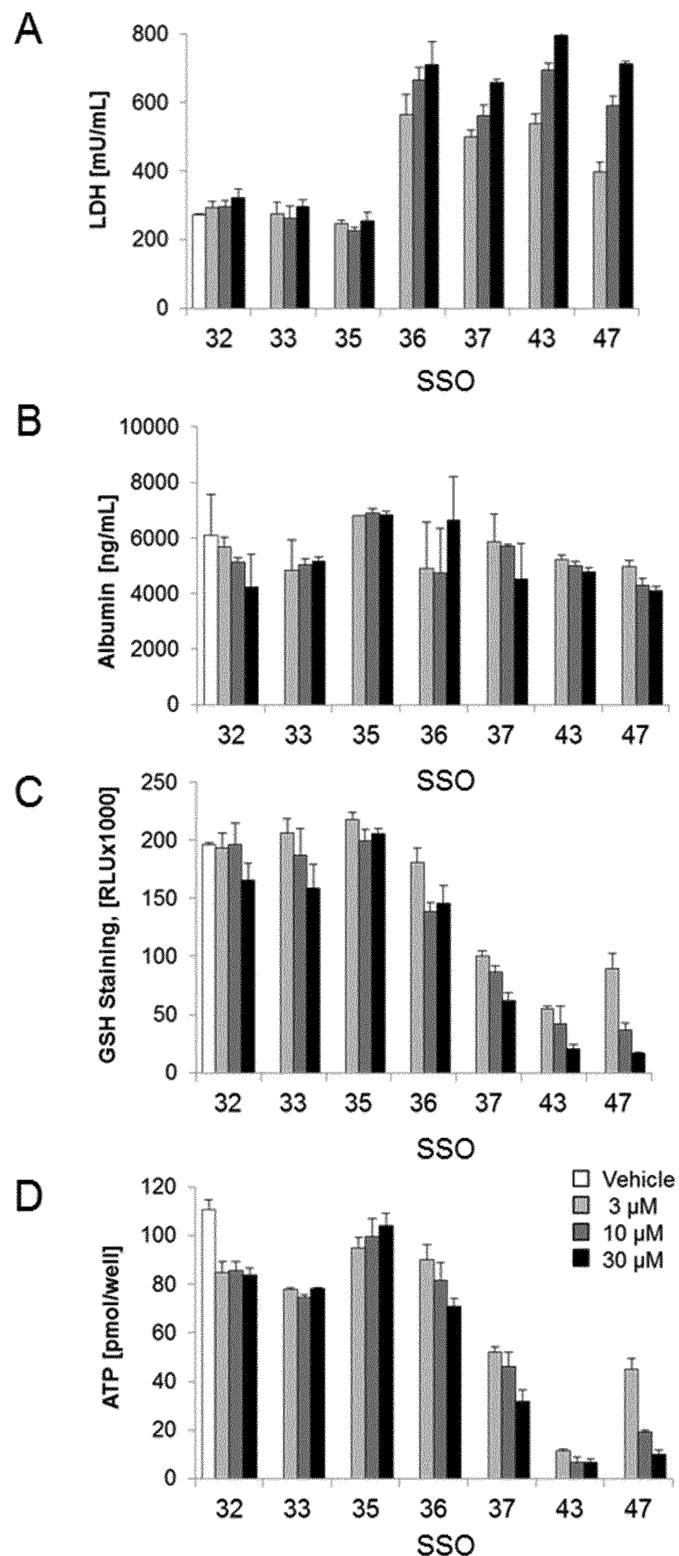
FIG. 2 ASO induced toxicity in primary mouse hepatocytes. Secreted LDH (A) and albumin (B) levels and intracellular GSH (C) and ATP (D) concentrations after 3 day treatment with a tool set of hepatotoxic and non-hepatotoxic ASOs. Data are means±StDev.

In some embodiments the conjugate moiety is or comprises a asialoglycoprotein receptor targeting moiety, which may include, for example galactose, galactosamine, N-formyl-galactosamine, Nacetylgalactosamine, N-propionyl-galactosamine, N-n-butanoyl-galactosamine, and N-isobutanoylgalactos-amine. In some embodiments the conjugate moiety comprises a galactose cluster, such as N-acetylgalactosamine trimer. In some embodiments, the conjugate moiety comprises a GalNAc (N-acetylgalactosamine), such as a mono-valent, di-valent, tri-valent of tetra-valent GalNAc. Trivalent GalNAc conjugates may be used to target the compound to the liver (see e.g. U.S. Pat. No. 5,994,517 and Hangeland et al., Bioconjug Chem. 1995 November-December; 6(6):695-701, WO2009/126933, WO2012/089352, WO2012/083046, WO2014/118267, WO2014/179620, & WO2014/179445), see specific examples in FIG. 2. These GalNAc references and the specific conjugates used therein are hereby incorporated by reference.

Stereodefined Oligonucleotides

In the context of the present invention the term "stereodfined" refers to oligonucleotides where at least one phosphorothioate internucleoside linkage present in the oligonucleotide has defined stereochemistry, i.e. either Rp or Sp. In some embodiments the all of the phosphorothioate internucleoside linkages in a stereodefined oligonucleotide may be stereodefined, i.e. each phosphorothioate internucleoside linkage is independently selected from the group consisiting of Rp and Sp phosphorothioate internucleoside linkages.

Typically, oligonucleotide phosphorothioates are synthesised as a random mixture of Rp and Sp phosphorothioate linkages (also referred to as a racemic mixture). In the present invention, gapmer phosphorothioate oligonucleotides are provided where at least one of the phosphorothioate linkages of the gap region oligonucleotide is stereodefined, i.e. is either Rp or Sp in at least 75%, such as at least 80%, or at least 85%, or at least 90% or at least 95%, or at least 97%, such as at least 98%, such as at least 99%, or (essentially) all of the oligonucleotide molecules present in the oligonucleotide sample. Such oligonucleotides may be referred as being stereodefined, stereoselective or stereospecified: They comprise at least one phosphorothioate linkage which is stereospecific. The terms stereodefined and stereospecified/stereoselective may be used interchangeably herein. The terms stereodefined, stereoselective and stereospecified may be used to describe a phosphorothioate internucleoside linkage (Rp or Sp), or may be used to described a oligonucleotide which comprises such a phosphorothioate internucleoside linkage. It is recognised that a stereodefined oligonucleotide may comprise a small amount of the alternative stereoisomer at any one position, for example Wan et al reports a 98% stereoselectivity for the gapmers reported in NAR, November 2014.

Immunotoxicity Biomarker Assay:

Also described herein is a method for predicting immunotoxicity of an oligonucleotide by measuring at least one complement biomarker and/or at least one (such as at least two) cytokine biomarkers in blood samples.

Also described herein is a method for predicting immunotoxicity of an oligonucleotide by measuring at least one complement biomarker and at least two cytokine biomarkers in blood samples.

In some embodiments, the method disclosed or claimed in the present application may be combined with the above method for predicting immunotoxicity of an oligonucleotides.

In some embodiments blood samples from at least 3 donors are used. Typically the blood is obtained from healthy donors. In some embodiments the blood sample from multiple donors are pooled. In some embodiments they are not pooled.

In some embodiments the method of the invention further includes or provides a method of predicting immunotoxicity comprising the steps of a) administering the oligonucleotide to human blood; b) incubating the samples between 30 min to 8 hours; c) stop the reaction; and d) measure at least two, three, four, five of or all of the following biomarkers:

complement biomarkers C3a and C5a, cytokine biomarkers interleukin 6 (IL6), interleukin 8 (IL8), tumor necrosis factor alpha (TNFa), and monocyte chemoattractant protein-1 (MCP1); wherein a mean increase above about 2 fold compared to a control in at least two of the biomarkers is indicative of [e.g. likely] in vivo immunotoxicity of the oligonucleotide. The blood sample of step a) is typically obtained from at least one healthy human subject, such as at least two or at least three healthy human subjects.

EXAMPLES

Example 1

Methods

Mouse Liver Perfusion and Hepatocyte and Nonparenchymal Cell Isolation

Permission for animal studies was obtained from the local regulatory agencies, and all study protocols were in compliance with the federal guidelines.

Primary mouse hepatocytes were isolated from 10- to 13-week old male C571316 mice by a retrograde two-step collagenase liver perfusion. Briefly, fed mice were anaesthetized with sodium pentobarbital (120 mg/kg, i.p.). Perfusion tubing was inserted via the right ventricle into the v. cava caudalis. Following ligation of the v. cava caudalis distal to the v. iliaca communis, the portal vein was cut and the two-step liver perfusion was started. The liver was first perfused for 5 min with a pre-perfusing solution consisting of calcium-free, EGTA (0.5 mM)-supplemented, HEPES (20 mM)-buffered Hank's balanced salt solution, followed by a 12-min perfusion with NaHCO3 (25 mM)-supplemented Hank's solution containing CaCl2 (5 mM) and collagenase (0.2 U/ml; Collagenase Type II, Worthington). Flow rate was maintained at 7 ml/min and all solutions were kept at 37° C. After in situ perfusion, the liver was excised, the liver capsule was mechanically opened, the cells were suspended in William's Medium E (WME) without phenol red (Sigma W-1878), and filtered through a set of nylon cell strains (40- and 70-mesh). Dead cells were removed by a Percoll (Sigma P-4937) centrifugation step (percoll density: 1.06 g/ml, 50 g, 10 min) and an additional centrifugation in WME (50xg, 3 min).

The supernatant from the hepatocytes sedimentation step was kept for the isolation of the non parenchymal cell (NPC) fraction. Cells were pelleted by a centrifugation step (1200 rpm, 10 min, Eppendorf 5810R) and resuspended in 12 mL William's Medium E (WME) without phenol red (Sigma W-1878). NPCs were isolated by a Percoll gradient (23% (upper phase) and 50% (bottom phase); Sigma P-4937) centrifugation step (Percoll density: 1.06 g/ml, 1350 g, 10 min, brake off). Cells were washed once in WME, centrifuged (200 g, 5 min, Eppendorf 5810R) and resuspended in 13 mL William's Medium E (WME) containing 10% fetal calf serum, penicillin (100 U/ml), streptomycin (0.1 mg/ml).

Hepatocyte Culturing and Oligonucleotide Treatment

Freshly isolated primary mouse or cryopreserved human (BioreclamationIVT, Brussels, Belgium) hepatocytes were suspended in WME supplemented with 10% fetal calf serum, penicillin (100 U/ml), streptomycin (0.1 mg/ml) at a density of approx. 5×106 cells/ml and seeded into collagen-coated 96-well plates (Becton Dickinson AG, Allschwil, Switzerland) at a density of $0.25\times10^5$cells/well (mouse) and $0.4\times10^5$cells/well (human). Cells were pre-cultured for 3 to 4 h allowing for attachment to cell culture plates before start of treatment with oligonucleotides. Seeding medium was replaced by 90 µl of serum free WME and 10 µl of oligonucleotide stock solutions in PBS were added to the cell culture and left on the cells for 3 days.

For co-cultures, mouse NPCs were plated into collagen-coated 96-well plates (Becton Dickinson AG, Allschwil, Switzerland). After 30 min, primary mouse hepatocytes, suspended in WME supplemented with 10% fetal calf serum, penicillin (100 U/ml), streptomycin (0.1 mg/ml) at a density of $0.25\times10^5$ cells/well, were seeded on top of the NPC layer. Cells were cultured for 3 to 4 h allowing for attachment to cell culture plates before start of treatment with oligonucleotides as described above.

Other Cell Types

Primary mammalian hepatocytes are obtain from living animals, and it is therefore desirable to find an alternative cell types which can be used in the method of the invention in place of the primary mammalian hepatocytes, without the need to use primary cells.

In addition to mammalian primary mammalian hepatocyte mono and co-cultures, we also used a variety of other cell types, including 3T3 fibroblasts and human HepG2 cells. As has been previously reported, the use of in vitro assays into these established cell lines did not give a biomarker response which was predictive of in vivo toxicity, even when using the gymnotic delivery method.

We have also investigated the use of hepatocytes derived from induced pluripotent stem cells (iPS cells), and may be used in place of the primary mammalian hepatocytes. our initial results indicate that the use of such cells are useful in predicting in vivo toxicity, and as such in some embodiments, hepatocyte cells derived from induced pluripotent stem cells (iPS cells)cells may be used in place of the primary mammalian hepatocytes in the methods of the invention. Hepatocytes derived from induced pluripotent stem cells (iPS cells) are commercially available (e.g.

ReproHepato™ cells available from Stemgent, oriCell® Hepatocytes, available from Cellular Dynamics Int.). See also Takayama et al., Molecular Therapy (2012); 20 1, 127-137 which describes the efficient generation of functional hepatocytes from human embryonic stem cells and induced pluripotent stem cells by HNF4a transduction.

RNA Isolation and qPCR mRNA purification from mouse hepatocytes was performed using the RNeasy 96 Kit (Qiagen, Hombrechtikon, Switzerland) including an RNAse free DNAse I treatment according to the manufacturer's instructions. cDNA was synthesized using iScript single strand cDNA Synthesis Kit (Bio-Rad Laboratories AG, Rheinach, Switzerland). Quantitative real-time PCR assays (qRT-PCR) were performed using the Roche SYBR Green I PCR Kit and the Light Cycler 480 (Roche Diagnostics, Rotkreuz, Switzerland) with specific DNA primers. Analysis was done by the ΔΔCt threshold method to determine expression relative to RPS12 mRNA. Each analysis reaction was performed in duplicate, with two samples per condition.

LDH, Albumin, GSH and ATP Assays

Lactate dehydrogenase (LDH) released into the culture media was determined using a Cytotoxicity Detection Kit (Roche 11644793001, Roche Diagnostics GmbH Roche Applied Science Mannheim, Germany) according to the manufacturer's protocol. Albumin secretion was quantitated using mouse albumin ELISA Kit from Alpco diagnostics (41-ALBMS-E01). Intracellular GSH levels were determined in intact cells by a fluorescent assay using Monochlorobimane (Fluka, 69899). In brief after removal of the cell supernatant, 100 μl of Krebs Henseleit Buffer (KHB) was added to the wells and background fluorescence was recorded. Next 50 μl of a 300 μM solution of monochlorobimane dissolved in KHB was added to the cells and incubated for 15 min at 37° C., before the reaction was stopped by removal of the monochlorobimane solution and addition of 100 μL of fresh KHB to each well. Fluorescence was measured using a VictorV3 reader. For the determination of cellular ATP levels the CellTiter-Glo® Luminescent Cell Viability Assay (G9242, Promega Corporation, Madison Wis., USA) was used according to the manufacturer's protocol. Each sample was tested in triplicate.

Apoptosis Assay

Caspase 3/7 activity was determined using the Caspase Glo 3/7 Assay (Promega Corporation, Madison Wis., USA). In brief, Caspase Glo reagent was added to the cells at indicated time points, incubated for 30 min, before luminescence was determined on an Enspire multi-mode plate reader (Perkin Elmer) according to the manufacturer's instructions.

Cytokine Measurement

25 μl of supernatants from hepatocyte/NPC co-cultures were collected after 24, 48 and 64 hours of LNA treatment and stored at −20° C. until analysis. For cytokine profiling, supernatants were thawed on ice, diluted 2× in sample dilution buffer (BioRad catalog #M60-009RDPD) and analyzed by multiplex ELISA using a mouse cytokine 23-plex (Bio-Plex Pro Mouse Cytokine 23-plex Assay, catalog #M60009RDPD) and Bio-Plex® 200 Systems (BioRad) according to the manufacturer's instructions. The 23 analytes were: IL-1α, IL-1β, IL-2, IL-3, IL-4, IL-5, IL-6, IL-9, IL-10, IL-12 (p40), IL-12 (p70), IL-13, IL-17A, Eotaxin, G-CSF, GM-CSF, IFN-γ, KC, MCP-1, MIP-1α, MIP-1β, RANTES and TNF-α. Data of selected analytes are reported as average concentrations and standard deviations of triplicate wells.

miRNA Analysis

To isolate miRNAs, 70 ul of cell culture supernatants (SN) were collected and the RNA was isolated using the miRNeasy Mini Kit (Qiagen, Germany) following the manufacturer's instructions. A volume of 1 ul of RNA was used for the cDNA synthesis using the cDNA TaqMan® MicroRNA Reverse Transcription kit (Applied Biosystems, Thermo Fischer Scientific, USA) and the expression of miR-122 was determined using a TaqMan miRNA assay (hsa-miR-122-5p; Applied Biosystems, Thermo Fischer Scientific, USA). Briefly, each sample was analyzed in duplicates and the reactions were performed using 1.33 μL of cDNA in a final volume of 20 μL with TaqMan® Fast Advanced Master Mix reagents (Applied Biosystems, Thermo Fischer Scientific, USA). The PCR conditions were standardized to 95° C. for 20 s followed by 40 cycles of 95° C. for 1 s and 60° C. for 20 s. The reactions were carried out on a QuantStudio 12K Flex Real-Time PCR System (Applied Biosystems, Lyfe technologies, USA), the EDS files were loaded in to the Quantstudio 12K Flex Software v1.2.2 and the raw Ct values were calculated using automatic baseline and fixed threshold values. The fold changes in microRNA expression were calculated according to the ΔΔCt-method, using spiked-in ath-miR-159 for normalization (Livak and Schmittgen, 2001).

Example 2

For evaluation and validation of potential predictive in vitro hepatotoxicity assays a set of ASOs with known in vivo hepatotoxicity was selected. These ASOs had LNA-modified nucleotides in the wings (LNA gapmers) and were directed against mouse myd88 mRNA (Table 1). Oligonucleotides were tested in freshly isolated primary mouse hepatocytes for 2-3 days without any carrier or transfection reagent (gymnosis). In order to determine whether the oligonucleotides were taken up by cells the target knockdown after 48 hours of treatment was determined. A clear reduction in myd88 mRNA by 50-90% in primary hepatocytes treated with ASOs 32, 33, 35, 36, 37, 43 and 47 was observed indicating target engagement (FIG. 1

TABLE 1

| ASO | SEQ ID No | ALT [U/L] | Sequence |
|---|---|---|---|
| 32 | 1 | 64 | 5'-${}^{m}C^{o}_{S}$ $A^{o}_{S}$ $A^{o}_{S}$ $a_{S}$ $g_{S}$ $g_{S}$ $a_{S}$ $a_{S}$ $a_{S}$ $c_{S}$ $a_{S}$ $c_{S}$ $a_{S}$ ${}^{m}C^{o}_{S}$ $A^{o}_{S}$ $T^{o}$-3' |
| 33 | 2 | 59 | 5'-${}^{m}C^{o}_{S}$ $A^{o}_{S}$ $A^{o}_{S}$ $a_{S}$ $t_{S}$ $g_{S}$ $c_{S}$ $t_{S}$ $g_{S}$ $a_{S}$ $a_{S}$ $a_{S}$ $c_{S}$ $T^{o}_{S}$ $A^{o}_{S}$ $T^{o}$-3' |
| 35 | 3 | 67 | 5'-${}^{m}C^{o}_{S}$ $T^{o}_{S}$ ${}^{m}C^{o}_{S}$ $a_{S}$ $a_{S}$ $c_{S}$ $a_{S}$ $t_{S}$ $c_{S}$ $a_{S}$ $a_{S}$ $g_{S}$ $c_{S}$ $A^{o}_{S}$ $G^{o}_{S}$ $T^{o}$-3' |
| 36 | 4 | 1889 | 5'-$A^{o}_{S}$ ${}^{m}C^{o}_{S}$ $T^{o}_{S}$ $g_{S}$ $c_{S}$ $t_{S}$ $t_{S}$ $t_{S}$ $c_{S}$ $c_{S}$ $a_{S}$ $c_{S}$ $t_{S}$ ${}^{m}C^{o}_{S}$ $T^{o}_{S}$ $G^{o}$-3' |
| 37 | 5 | 2368 | 5'-$G^{o}_{S}$ ${}^{m}C^{o}_{S}$ ${}^{m}C^{o}_{S}$ $t_{S}$ $c_{S}$ $c_{S}$ $c_{S}$ $a_{S}$ $g_{S}$ $t_{S}$ $t_{S}$ $c_{S}$ $c_{S}$ $T^{o}_{S}$ $T^{o}_{S}$ $T^{o}$-3' |
| 43 | 6 | 1890 | 5'-$G^{o}_{S}$ $A^{o}_{S}$ $T^{o}_{S}$ $g_{S}$ $c_{S}$ $c_{S}$ $t_{S}$ $c_{S}$ $c_{S}$ $c_{S}$ $a_{S}$ $G^{o}_{S}$ $T^{o}_{S}$ $T^{o}$-3' |

TABLE 1-continued

| ASO | SEQ ID No | ALT [U/L] | Sequence |
|---|---|---|---|
| 47 | 7 | ND | 5'-$G^o{}_S$ $A^o{}_S$ $c_S$ $a_S$ $t_S$ $t_S$ $g_S$ $c_S$ $c_S$ $t_S$ $^mC^o{}_S$ $T^o{}_S$ $A^o$-3' |

Table 1 Selection of tool ASOs with documented in vivo hepatotoxicity (ALT levels after 2 week treatment in mice with 5 × 15 mg/kg tail vein injection) that were used for the validation of in vitro hepatotoxicity assays.
ND: no ALT levels were determined, since group had to be sacrificed early due to severe toxicity.
Small letters: nucleotides;
s: phosphorothioate backbone;
Capital letters: locked nucleic acids (LNA),
$^o$: oxy-LNA
$^m$C: methylated cytosine.

Example 3

The effect of in vivo safe and toxic oligonucleotides on hepatocyte function and cell viability was assessed in vitro by determination of albumin secretion and LDH levels in the supernatant as well as intracellular GSH levels and cellular ATP content. After 2 days of incubation of cells with the respective oligonucleotides no significant changes in hepatocyte function or viability was observed (data not shown). After 3 days of treatment, LDH levels were clearly increased in supernatants of cells treated with toxic ASOs 36, 37, 43 and 47, while no change in LDH levels was seen with safe oligonucleotides 32, 33 and 35 (FIG. 2A). In contrast, albumin secretion was not notably changed compared to vehicle treated hepatocytes for all ASOs tested indicating that this may not be a sensitive marker for oligonucleotide induced toxicity in this setting (FIG. 2B). In order to assess the potential of ASOs to induce oxidative stress, intracellular GSH content was determined after 3 day treatment. Hepatotoxic ASOs 37, 43 and 47 induced a clear reduction in glutathione levels in mouse hepatocyte cultures and ASO 36 showed a very mild reduction in GSH. Safe ASOs 32, 33 and 35 did not change GSH levels compared to vehicle (FIG. 2C). A similar picture was obtained when assessing intracellular ATP levels which clearly revealed a differentiation between toxic and safe ASOs. Cellular ATP levels were slightly reduced in hepatocytes treated with safe ASOs 32, 33 and 35 compared to the vehicle group, but this effect was small and not concentration-dependent. Treatment with hepatotoxic ASOs, 37, 43 and 47 led to a marked reduction in ATP while ASO 36 showed a concentration dependent mild reduction in intracellular ATP concentration (FIG. 2D).

Example 4

Figure 3:
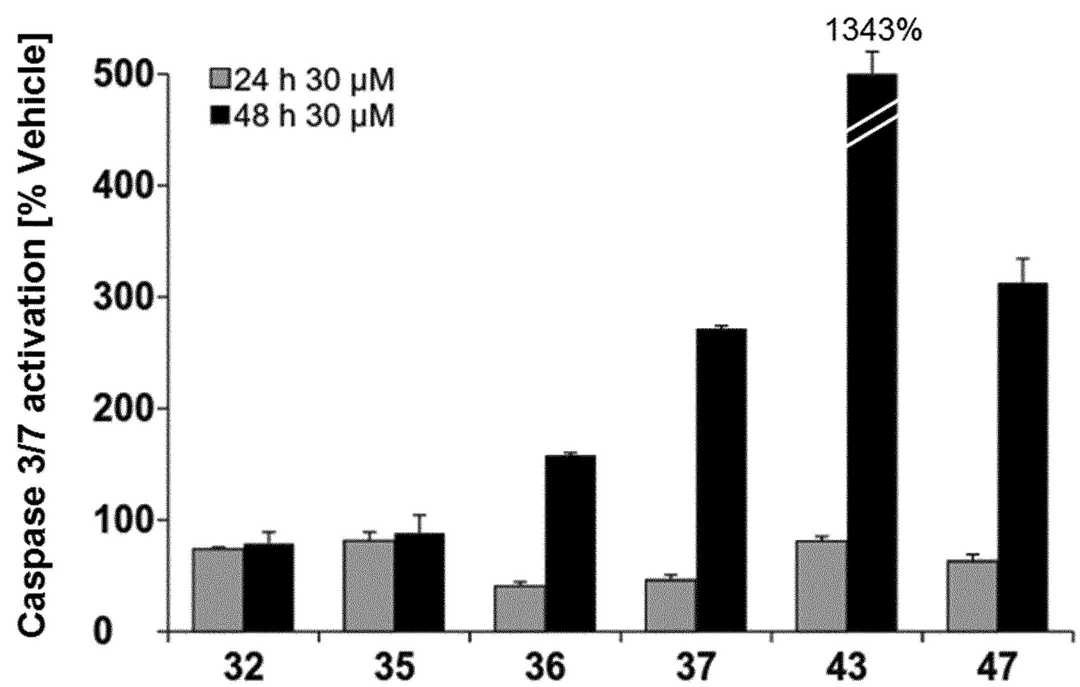
FIG. 3 Apoptosis induced by ASOs in primary mouse hepatocytes. Changes in caspase-3/7 activation in primary mouse hepatocytes after 24 and 48 h of incubation with the respective ASO at 30 μM. Data are normalized to vehicle treated cells. Data are means±StDev FIG. 4 ASO induced toxicity in primary mouse hepatocyte NPC co-cultures. Secreted LDH (A) and albumin (B) levels and intracellular GSH (C) and ATP (D) concentrations after 3 day treatment of mouse primary hepatocyte NPC co-cultures with a tool set of hepatotoxic and non-hepatotoxic ASOs. Data are means±StDev FIG. 5 ASO induced cytokine secretion in primary mouse hepatocyte NPC co-cultures. Secretion of MIP1a (A) and 11_1a (B) after 24, 48 and 64 hour treatment of primary mouse hepatocyte NPC co-cultures with safe ASO 32 and hepatotoxic ASOs 36, 43 and 47. Data are means±StDev.

ASO-mediated effect on apoptosis by measuring Caspase-3/7 activation was assessed at 3 different time points. After 24 hours of incubation, no activation of Caspase-3/7 could be detected (FIG. 3). At 48 hours, a clear increase in Caspase 3/7 activation was observed with toxic ASOs 36, 37, 43 and 47, with the strongest response induced by ASO 43, while no effect was seen with safe ASOs 32 and 35. After 3 days of treatment caspase activation could still be seen with toxic oligonucleotides (not shown). These signals were perfectly correlated with the cytotoxicity profile after 3 days treatment with ASOs. These results clearly indicate that hepatotoxic ASOs induce apoptosis in mouse hepatocytes, which then finally lead to the changes in cell viability shown in FIG. 2.

Example 5

Figure 4:
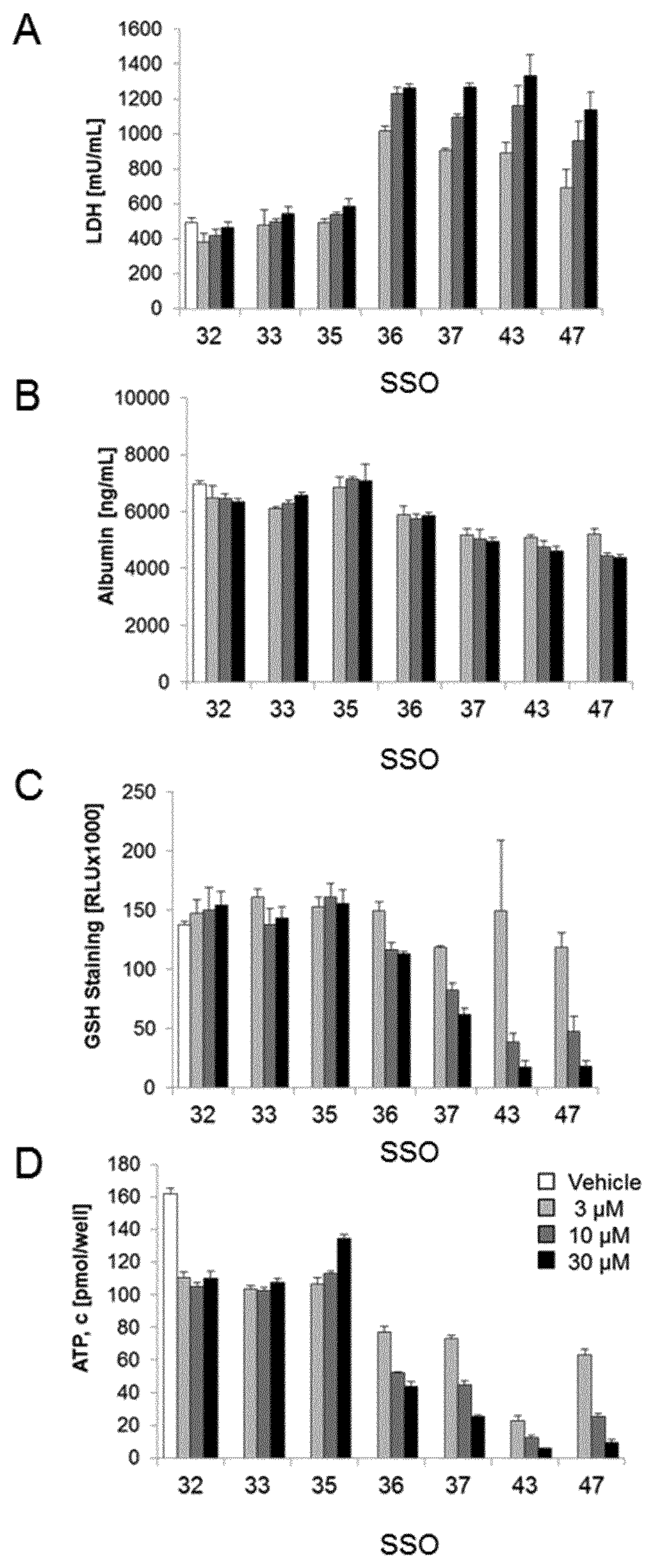

Hepatocyte non-parenchymal cell (NPC) co-cultures treated with hepatotoxic ASOs 36, 37, 43 and 47 for 3 days showed increased LDH levels (FIG. 4 A), slightly decreased albumin secretion (FIG. 4B), and a clear reduction in intracellular GSH levels (FIG. 4C) and ATP content (FIG. 4D) compared to vehicle treated co-cultures. None of these parameters was changed when cells were incubated with safe ASOs 32, 33 and 35. Compared to the results obtained with mouse hepatocyte monocultures, the co-cultures displayed similar sensitivity towards toxic and non-toxic ASOs as reflected by changes in LDH, GSH and ATP induced by toxic oligonucleotides.

Example 6

Figure 5:
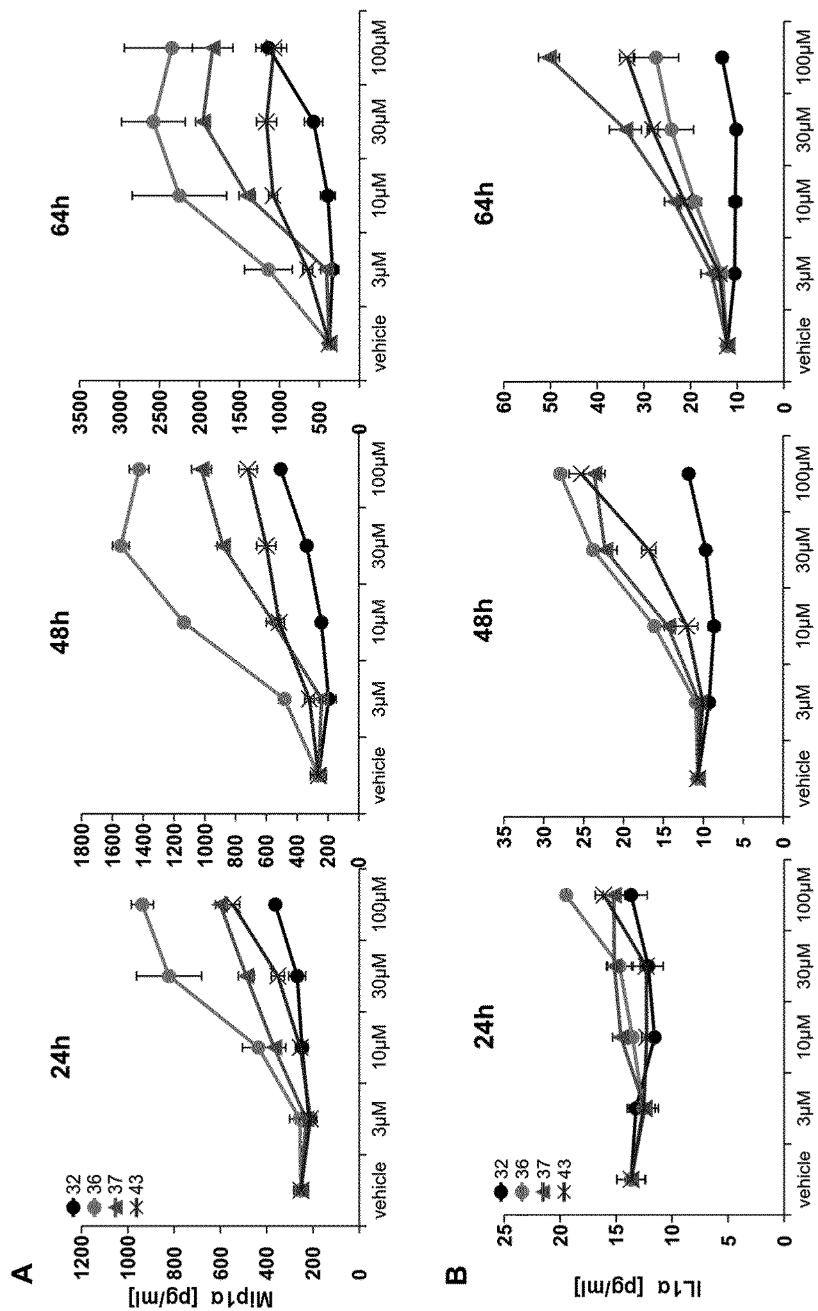

Changes in secreted cytokines and mir-122, an hepatocyte-specific marker for tissue damage (Wang K, Zhang S, Marzolf B, Troisch P, Brightman A, Hu Z, et al. Proc Natl Acad Sci USA. 2009; 106: 4402-4407. Filipowics, W. and Grosshans, H. (2011). Prog. Drug Res. 67, 221-238), were investigated upon ASO treatment. A subset of safe (32) and hepatotoxic ASOs (36, 37 and 43) was selected and the cytokine secretion profile using a multiplex luminex assay was determined after 1, 2 and 3 days of ASO treatment. Of the 23 tested analytes (see under Cytokine measurement above), Macrophage Inflammatory Protein 1 alpha (MIP1a) and Interleukin 1 alpha (IL1a) showed a time-dependent response in cells treated with hepatotoxic ASOs. As shown in FIG. 5, MIP1a was already induced up to 5 fold after 24 hours of treatment with toxic ASOs 36, 37 and 43. We also observed an increase in IL1a with toxic ASO with a later onset than MIP1a, clearly separating toxic and non-toxic ASO at 48 and 64 hours.

Figure 6:
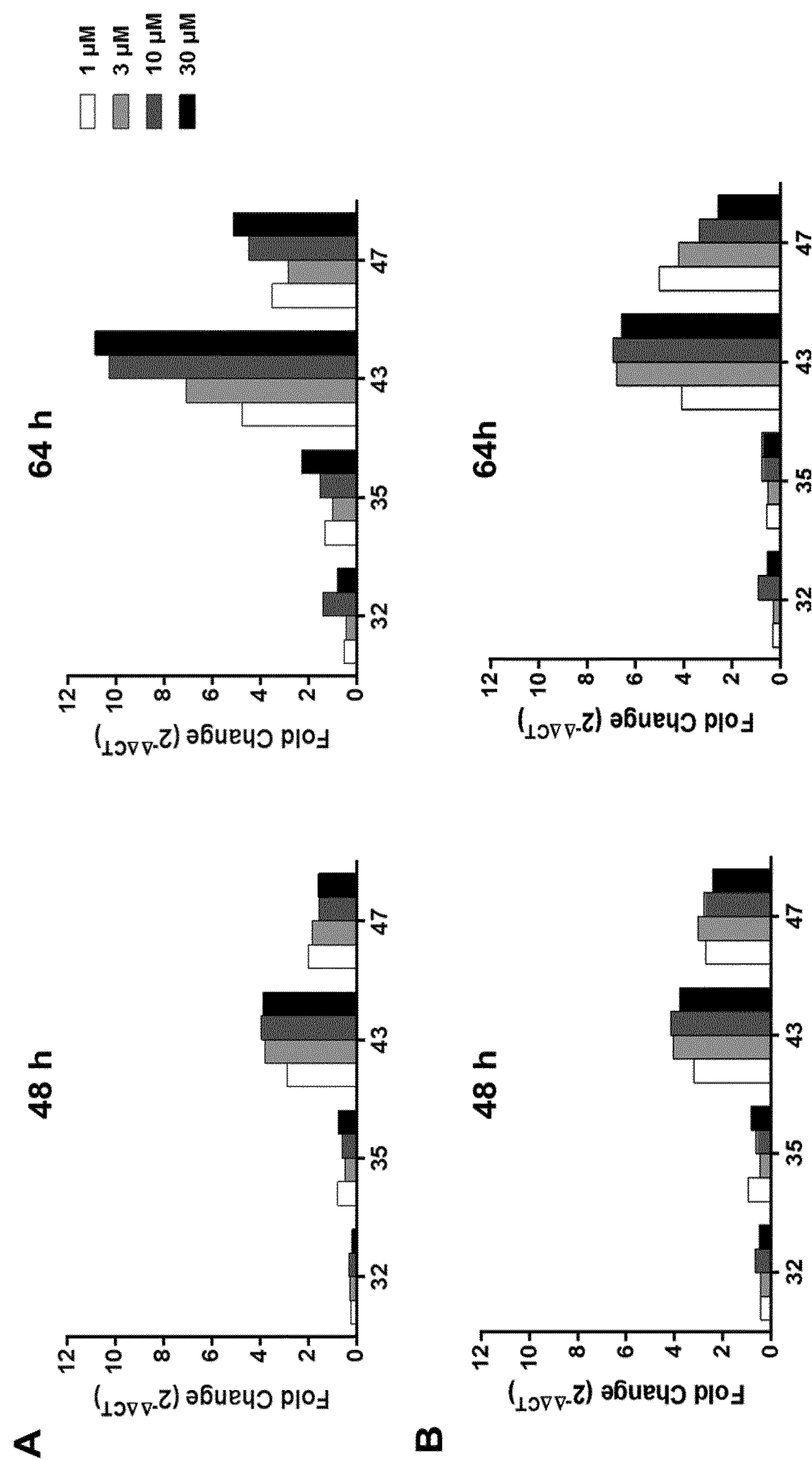
FIG. 6 miR-122 release. Mouse hepatocyte-NPC co-cultures (A) or hepatocyte monocultures (B) were treated with the respective ASOs for 48 or 64 hours and cell-free supernatant was collected. The levels of miR-122 at 48 h and 64 h were assessed using real-time qPCR. miRNA levels were normalized to vehicle treated cells.

Example 7 miR122-release in the supernatants was investigated in hepatocyte-NPC co-cultures treated with non-toxic ASO 32 and 35 and toxic ASOs 43 and 47. Increases in miR122 were already observed after 2 days of treatment with toxic ASOs (FIG. 6). Although a 10 fold increase in miR122 was detected in the supernatants of the co-cultures (FIG. 6A), the amount was not significantly higher than the miR-122 release observed when the hepatocytes were cultured alone (FIG. 6B). Overall, these mechanistic readouts further support the idea that the liver injury observed in vivo is a result of a direct hepatocellular damage rather than non-parenchymal cell mediated event.

Example 8

34 ASOs targeting different mRNAs and showing a broad spectrum of mouse in vivo hepatotoxicity were tested in the in vitro hepatotoxicity assay. Cellular ATP and secreted LDH were selected as readouts after 3 days of treatment in freshly isolated mouse hepatocyte monocultures, as these two assay turned out to be sufficient to recapitulate the in vivo toxicity pattern with our initial set of tool ASOs. As shown in FIG. 7 with this broad set of oligonucleotides, there is a good correlation of the in vivo hepatotoxicity with in vitro readouts, with ASOs that induced increases in plasma ALT levels in vivo also clearly showing an increase in LDH and a reduction in ATP levels in vitro. Thus this assay can be suitable to predict the hepatotoxic potential of newly synthesized oligonucleotides prior to moving into first in vivo studies.

Example 9

A similar protocol was established for human primary hepatocytes. Cytotoxicity readouts were measured 3 days after treatment with the myd88 tool ASOs, initially tested in primary mouse hepatocytes. A clear pattern reflecting in vivo innocuous versus in vivo hepatotoxic ASOs in human hepatocytes was obtained for 5 out of the 7 tested myd88 tool compounds in human hepatocytes (FIG. 8A). Toxic ASOs 37 and 43 showed a dose dependent increase in LDH levels and decrease in intracellular ATP levels, whereas ASOs 32, 33 and 35 had no apparent effect. Two reference ASOs, an anti-survivin oligonucleotide (see Raetz et al., J Pediatr Hematol Oncol. 2014 August; 36(6):458-63 and WO2006/050732) and an anti Bcl2 oligonucleotide (see Frieden and Orum., (Drugs. 2006 October; 9(10):706-11 and WO2005/061710) with documented pre-clinical as well as clinical liver liability were tested in mouse (FIG. 8B) and human primary hepatocytes (FIG. 8C). With both ASOs, increases in LDH levels and reduction in cellular ATP were observed in mouse and human cellular systems, suggesting reliability of the human hepatocyte assay for estimation of a potential clinical liver toxicity risk.

Example 10

Stereodefined Oligonucleotide In Vitro Toxicity Screening in Primary Hepatocytes Methodology: See Example 1.

| Compounds used (SEQ ID NO 8) | |
|---|---|
| 5'-$^{m}C_{x}A_{x}{}^{m}C_{x}a_{x}t_{x}t_{x}c_{x}c_{x}t_{x}t_{x}g_{x}c_{x}t_{x}{}^{m}C_{x}T_{x}G$-3' | (Parent #56) |
| 5'-$^{m}C_{x}A_{x}{}^{m}C_{x}a_{x}t_{x}t_{s}c_{x}c_{x}t_{x}t_{s}g_{x}c_{x}t_{s}{}^{m}C_{x}T_{s}G$-3' | (Comp #57) |
| 5'-$^{m}C_{x}A_{x}{}^{m}C_{x}a_{x}t_{x}t_{r}c_{x}c_{x}t_{x}t_{r}g_{x}c_{x}t_{r}{}^{m}C_{x}T_{r}G$-3' | (Comp #58) |
| 5'-$^{m}C_{x}A_{x}{}^{m}C_{x}a_{x}t_{x}t_{s}c_{s}c_{x}t_{x}t_{s}g_{s}c_{x}t_{x}{}^{m}c_{x}T_{x}G$-3' | (Comp #59) |
| 5'-$^{m}C_{x}A_{x}{}^{m}C_{x}a_{x}t_{x}t_{r}c_{r}c_{x}t_{x}t_{r}g_{r}c_{x}t_{x}{}^{m}C_{x}T_{x}G$-3' | (Comp #60) |

Capital letters are beta-D-oxy LNA nucleosides, small letters are DNA nucleosides Subscript x=randomly incorporated phosphorothioate linkage from a racemic mixture of Rp and Sp monomers.

Subscript s=stereocontrolled phosphoramidite linkage from a Sp monomer

Subscript r=stereocontrolled phosphoramidite linkage from a Rp monomer

Superscript m preceding a capital C represents 5-methyl cytosine LNA nucleoside.

Target knock-down Analysis—See example 1

Figure 9:
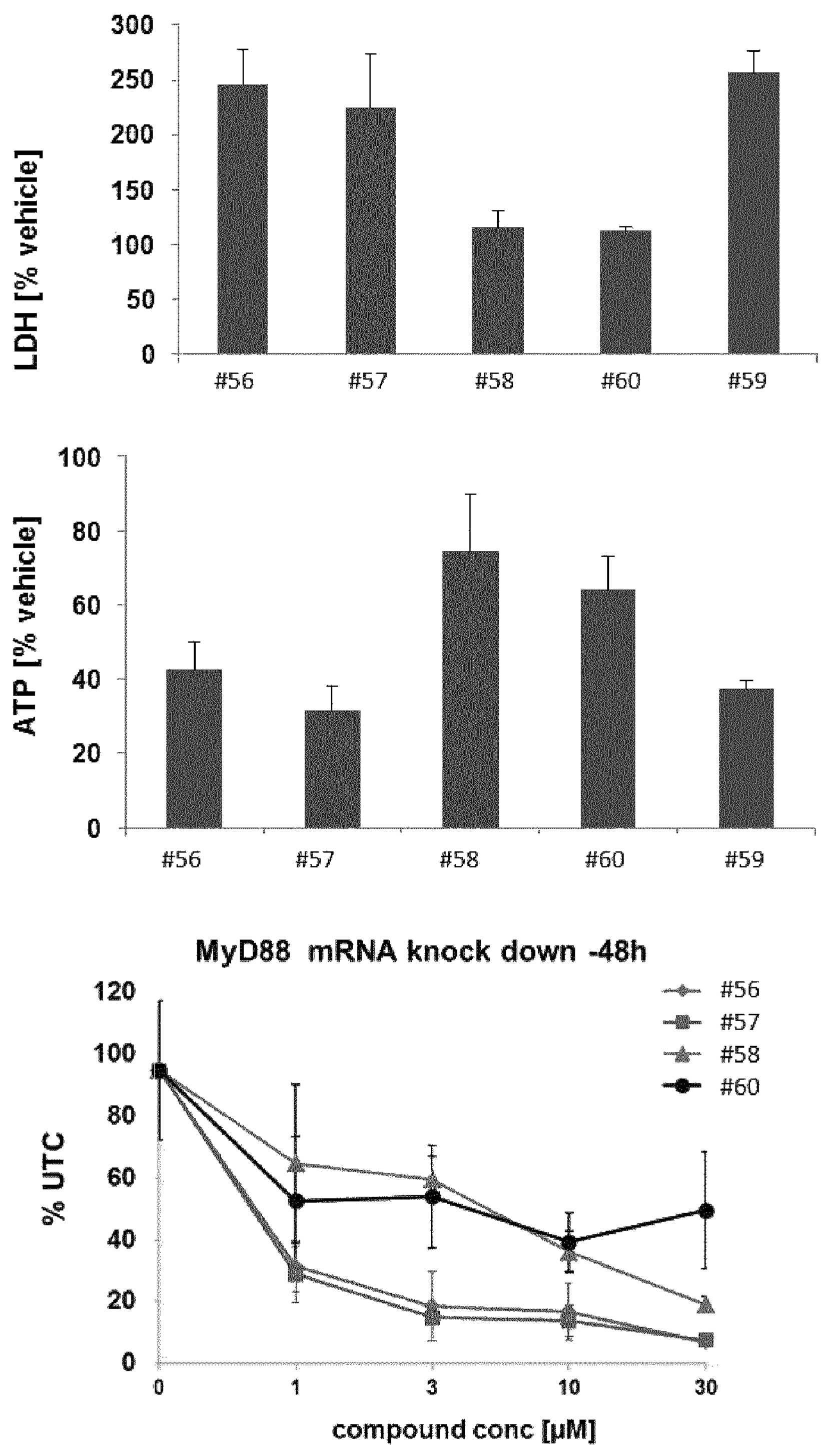
FIG. 9 Stereodefined ASOs—In vitro toxicity screening in primary mouse hepatocytes. Changes in LDH levels in the supernatants and intracellular ATP levels of cells treated for 3 days with the respective LNAs. Target knockdown (Myd88) was evaluated after 48 hours.

The results are shown in FIGS. 9 & 10. Compounds #58 and #60 have significantly reduced toxicity whilst retaining effective antisense activity against the target (Myd88). These compounds comprise Rp stereodefined phosphorothioate linkages.

The invention claimed is:

1. A method for predicting the in vivo toxicity of an oligonucleotide in a mammal, said method comprising the steps of:

a. administering the oligonucleotide to a population of primary mammalian hepatocyte cells or population of hepatocytes derived from induced pluripotent stem cells in vitro in a cell culture media;

b. culturing the cells in vitro in the cell culture media for a period of time; and c. subsequently measuring the level of lactate dehydrogenase (LDH) released into the culture media or measuring the level of cellular ATP levels;

wherein an increase in lactate dehydrogenase in the cell culture media, or a decrease in cellular ATP levels is indicative of an oligonucleotide which is hepatotoxic in vivo in the mammal.

2. The method according to claim 1, wherein the oligonucleotide is administered to the population of primary mammalian hepatocyte cells via gymnosis.

3. The method according to claim 1, wherein level of lactate dehydrogenase in the cell culture media or the level of intracellular ATP levels is compared to a reference value obtained from negative control sample.

4. The method according to claim 1, wherein step c) further comprises the measurement of the level of microRNA-122 released into the culture media.

5. The method according to claim 1, wherein step c) further comprises the measurement of intracellular glutathione (GSH) levels, wherein a reduction in GHS levels are indicative of an oligonucleotide which is hepatotoxic in vivo in the mammal.

6. The method according to claim 1, wherein the level of LDH present in the culture media is at least 20% higher as compared to the reference value.

7. The method according to claim 1, wherein the level of cellular ATP is at least 20% lower that the reference value.

8. The method according to claim 1, wherein the primary mammalian hepatocyte cells are selected from the group consisting of rodent primary hepatocyte cells; primate primary hepatocyte cells pig primary hepatocyte cells and dog primary hepatocyte cells.

9. The method according to claim 1, wherein the cells are cultured in step b) for a period of between 1 to 7 days.

10. The method according to claim 1, wherein the oligonucleotide comprises LNA or 2' modified nucleosides.

11. The method according to claim 1, wherein the oligonucleotide is a gapmer oligonucleotide.

12. The method according to claim 1, wherein the toxicity in vivo is hepatotoxicity.

13. A method for selecting one or more oligonucleotides suitable for in vivo administration to a mammal, from a library of oligonucleotides, said method comprising the steps of a. Obtaining a library of oligonucleotides
b. administering at least one member of the library of oligonucleotides to a population of primary mammalian hepatocyte cells in vitro via gymnosis;
c. culturing the cells in vitro for a period of time;
d. measuring the amount of at least one biomarker of toxicity for each oligonucleotide
e. selecting one or more oligonucleotides which is or is predicted to be not toxic and optionally administering the selected oligonucleotides in vivo to the mammal.

14. The method according to claim 13, wherein the library of oligonucleotides is a library of oligonucleotide variants (child oligonucleotides) of a parent oligonucleotide, wherein the parent oligonucleotide is toxic, and wherein step c. identifies one or oligonucleotide variants which are less toxic than the parent oligonucleotide; wherein the oligonucleotide variants retaining the core nucleobase sequence of the parent oligonucleotide.

15. The method according to claim 14, wherein the library of oligonucleotide variants comprises a population of child oligonucleotides which differ by virtue of the design of nucleoside modifications.

16. The method according to claim 15, wherein the library of child oligonucleotides are or comprise a population of child oligonucleotides with different gapmer designs, optionally including different mixed wing gapmer designs.

* * * * *

UNITED STATES PATENT AND TRADEMARK OFFICE

CERTIFICATE OF CORRECTION

PATENT NO. : 10,955,407 B2
APPLICATION NO. : 16/068963
DATED : March 23, 2021
INVENTOR(S) : Franziska Boess et al.

It is certified that error appears in the above-identified patent and that said Letters Patent is hereby corrected as shown below:

In the Claims

Column 51, Line 3, Claim 5, delete "GHS" and insert -- GSH --

Column 52, Line 15, Claim 14, delete "or" and insert -- or more --

Signed and Sealed this
Twenty-second Day of June, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 8

<210> SEQ ID NO 1
<211> LENGTH: 16
<212> TYPE: DNA
<213> ORGANISM: artificial
<220> FEATURE:
<223> OTHER INFORMATION: Oligonucleotide sequence

<400> SEQUENCE: 1

caaaggaaac acacat                                                  16


<210> SEQ ID NO 2
<211> LENGTH: 16
<212> TYPE: DNA
<213> ORGANISM: artificial
<220> FEATURE:
<223> OTHER INFORMATION: Oligonucleotide sequence

<400> SEQUENCE: 2

caaatgctga aactat                                                  16


<210> SEQ ID NO 3
<211> LENGTH: 16
<212> TYPE: DNA
<213> ORGANISM: artificial
<220> FEATURE:
<223> OTHER INFORMATION: Oligonucleotide sequence

<400> SEQUENCE: 3

ctcaacatca agcagt                                                  16
```

-continued

```
<210> SEQ ID NO 4
<211> LENGTH: 16
<212> TYPE: DNA
<213> ORGANISM: artificial
<220> FEATURE:
<223> OTHER INFORMATION: Oligonucleotide sequence

<400> SEQUENCE: 4

actgctttcc actctg                                                   16


<210> SEQ ID NO 5
<211> LENGTH: 16
<212> TYPE: DNA
<213> ORGANISM: artificial
<220> FEATURE:
<223> OTHER INFORMATION: Oligonucleotide sequence

<400> SEQUENCE: 5

gcctcccagt tccttt                                                   16


<210> SEQ ID NO 6
<211> LENGTH: 14
<212> TYPE: DNA
<213> ORGANISM: artificial
<220> FEATURE:
<223> OTHER INFORMATION: Oligonucleotide sequence

<400> SEQUENCE: 6

gatgcctccc agtt                                                     14


<210> SEQ ID NO 7
<211> LENGTH: 13
<212> TYPE: DNA
<213> ORGANISM: artificial
<220> FEATURE:
<223> OTHER INFORMATION: Oligonucleotide sequence

<400> SEQUENCE: 7

gacattgcct cta                                                      13


<210> SEQ ID NO 8
<211> LENGTH: 16
<212> TYPE: DNA
<213> ORGANISM: Artificial
<220> FEATURE:
<223> OTHER INFORMATION: Oligonucleotide sequence

<400> SEQUENCE: 8

cacattcctt gctctg                                                   16
```